United States Patent
Pastron

(10) Patent No.: US 10,702,638 B2
(45) Date of Patent: Jul. 7, 2020

(54) TRACHEAL AND PHARYNGEAL SUCTION DEVICE

(71) Applicant: NJR Medical, Inc., New York, NY (US)

(72) Inventor: Nicholas J. Pastron, New York, NY (US)

(73) Assignee: NJR MEDICAL, INC., New York, NY (US)

(*) Notice: Subject to any disclaimer, the term of this patent is extended or adjusted under 35 U.S.C. 154(b) by 0 days.

(21) Appl. No.: 16/120,160

(22) Filed: Aug. 31, 2018

(65) Prior Publication Data

US 2020/0069852 A1    Mar. 5, 2020

(51) Int. Cl.
*A61M 1/00* (2006.01)
*A61M 25/00* (2006.01)
*A61M 25/01* (2006.01)

(52) U.S. Cl.
CPC ........ *A61M 1/0086* (2014.02); *A61M 1/0039* (2013.01); *A61M 25/0074* (2013.01); *A61M 25/01* (2013.01); *A61M 2205/3327* (2013.01); *A61M 2210/065* (2013.01); *A61M 2210/1032* (2013.01)

(58) Field of Classification Search
CPC ...... A61B 17/3417; A61B 2017/00336; A61B 2018/0091; A61B 2018/00916; A61B 2018/0094; A61B 2018/00946; A61B 2018/00958; A61M 1/0039; A61M 1/0041; A61M 1/0043; A61M 1/0045; A61M 1/0047; A61M 1/0064; A61M 1/008; A61M 1/0086; A61M 2205/3327; A61M 2210/065; A61M 2210/1032; A61M 25/0074; A61M 25/01
See application file for complete search history.

(56) References Cited

U.S. PATENT DOCUMENTS

| | | | |
|---|---|---|---|
| 1,613,373 A | 1/1927 | Beck | |
| 2,127,215 A | 8/1938 | Gwathmey | |
| 2,756,742 A | 7/1956 | Barton | |
| 3,426,759 A * | 2/1969 | Smith | A61M 1/008 27/24.2 |
| 3,926,196 A | 12/1975 | Bornhorst et al. | |

(Continued)

FOREIGN PATENT DOCUMENTS

| EP | 1894585 A1 | 3/2008 |
|---|---|---|
| WO | 2013002832 | 1/2013 |

OTHER PUBLICATIONS

International Search Report and Written Opinion in Related PCT Application No. PCT/US2011/067741, dated Oct. 22, 2012, 26 pages.

(Continued)

*Primary Examiner* — Adam Marcetich
(74) *Attorney, Agent, or Firm* — Kilpatrick Townsend & Stockton LLP

(57) ABSTRACT

A tracheal and pharyngeal suction device includes a handle including an interior cavity within the handle body, a connector positioned within the interior cavity and moveable along at least a portion of a length of the interior cavity, a proximal suction catheter having a coupling portion and a treatment portion, wherein the coupling portion is coupled to a proximal side of the connector; and a distal suction catheter coupled to a distal side of the connector.

20 Claims, 22 Drawing Sheets

(56) References Cited

U.S. PATENT DOCUMENTS

| | | | |
|---|---|---|---|
| 3,937,220 A | 2/1976 | Coyne | |
| 4,041,937 A | 8/1977 | Diaz | |
| 4,148,308 A | 4/1979 | Sayer | |
| 4,204,328 A * | 5/1980 | Kutner | A61M 1/008 433/29 |
| 4,205,677 A * | 6/1980 | Engstrom | A61M 1/0047 433/95 |
| 4,213,451 A | 7/1980 | Swenson | |
| 4,306,547 A | 12/1981 | Lowell | |
| 4,487,600 A * | 12/1984 | Brownlie | A61M 1/008 433/95 |
| 4,729,765 A | 3/1988 | Eckels et al. | |
| 4,802,851 A | 2/1989 | Rhoades | |
| 4,878,900 A * | 11/1989 | Sundt | A61M 1/0039 604/119 |
| 4,883,426 A | 11/1989 | Ferrer | |
| 4,982,729 A | 1/1991 | Wu | |
| 5,000,754 A * | 3/1991 | DeOliveira | A61B 18/1402 606/42 |
| 5,013,300 A * | 5/1991 | Williams | A61M 1/008 433/91 |
| 5,025,806 A | 6/1991 | Palmer et al. | |
| 5,060,646 A | 10/1991 | Page | |
| 5,085,633 A | 2/1992 | Hanifl et al. | |
| 5,151,094 A | 9/1992 | Hanifl | |
| 5,215,522 A | 6/1993 | Page et al. | |
| 5,220,916 A | 6/1993 | Russo | |
| 5,378,226 A | 1/1995 | Hanifl et al. | |
| 5,394,865 A | 3/1995 | Salerno | |
| 5,694,922 A | 12/1997 | Palmer | |
| 5,730,727 A | 3/1998 | Russo | |
| 5,836,918 A | 11/1998 | Dondlinger | |
| 5,845,634 A | 12/1998 | Parker | |
| 5,855,562 A * | 1/1999 | Moore | A61M 1/0047 433/91 |
| 5,995,875 A * | 11/1999 | Blewett | A61B 18/1477 606/41 |
| 6,012,451 A | 1/2000 | Palmer | |
| 6,162,170 A | 12/2000 | Foley et al. | |
| 6,176,823 B1 | 1/2001 | Foley et al. | |
| 6,176,824 B1 | 1/2001 | Davis | |
| 6,238,213 B1 | 5/2001 | Young et al. | |
| 6,277,200 B2 | 8/2001 | Xia et al. | |
| 6,293,945 B1 * | 9/2001 | Parins | A61B 18/1402 606/45 |
| 6,500,142 B1 | 12/2002 | Harreld et al. | |
| 6,843,769 B1 | 1/2005 | Gandarias | |
| 6,986,757 B1 | 1/2006 | Kumasaki et al. | |
| 7,827,985 B2 | 11/2010 | Pastron | |
| 8,715,171 B2 | 5/2014 | Pastron | |
| 8,998,806 B2 | 4/2015 | Pastron | |
| 2001/0051783 A1 * | 12/2001 | Edwards | A61B 18/1477 604/22 |
| 2002/0108614 A1 * | 8/2002 | Schultz | A61M 1/0047 128/207.14 |
| 2004/0019256 A1 | 1/2004 | Cubb et al. | |
| 2004/0162553 A1 * | 8/2004 | Peng | A61B 18/1402 606/42 |
| 2005/0065411 A1 | 3/2005 | Baldwin et al. | |
| 2005/0090712 A1 | 4/2005 | Cubb | |
| 2005/0154379 A1 * | 7/2005 | McGowan, Sr. | A61F 9/008 606/4 |
| 2005/0240081 A1 | 10/2005 | Eliachar | |
| 2005/0273063 A1 * | 12/2005 | Hoell | A61M 1/0039 604/317 |
| 2005/0279359 A1 * | 12/2005 | LeBlanc | A61M 25/0111 128/207.14 |
| 2006/0036133 A1 | 2/2006 | Demsky | |
| 2006/0065268 A1 | 3/2006 | Koyama et al. | |
| 2006/0200183 A1 * | 9/2006 | Gardocki | A61B 17/0218 606/190 |
| 2007/0093693 A1 | 4/2007 | Geist et al. | |
| 2007/0106122 A1 | 5/2007 | Yokota | |
| 2007/0173764 A1 * | 7/2007 | Greeson | A61M 1/008 604/171 |
| 2007/0272258 A1 | 11/2007 | Pastron | |
| 2008/0145815 A1 * | 6/2008 | Hershey | A61C 1/16 433/91 |
| 2009/0281386 A1 * | 11/2009 | Acosta | A61B 17/3421 600/114 |
| 2011/0060192 A1 | 3/2011 | Pastron | |
| 2013/0006057 A1 | 1/2013 | Pastron | |
| 2013/0131615 A1 * | 5/2013 | Riordan | A61M 1/0039 604/319 |
| 2013/0303979 A1 * | 11/2013 | Stieglitz | A61M 1/0047 604/30 |
| 2014/0100584 A1 * | 4/2014 | Konstorum | A61F 11/002 606/109 |
| 2014/0221909 A1 * | 8/2014 | Burrow | A61M 1/0062 604/28 |
| 2015/0359950 A1 | 12/2015 | Salehi | |
| 2017/0112490 A1 * | 4/2017 | Purnell | A61M 1/0001 |
| 2017/0216092 A1 * | 8/2017 | Singh | A61B 17/3478 |
| 2018/0214217 A1 * | 8/2018 | Rodriguez | A61B 5/062 |
| 2019/0038817 A1 | 2/2019 | Forsberg et al. | |

OTHER PUBLICATIONS

Non-Final Office Action in related U.S. Appl. No. 13/171,151, dated May 30, 2013, 9 pages.

Response in related U.S. Appl. No. 13/171,151 dated Aug. 30, 2013, 15 pages.

Notice of Allowance in related U.S. Appl. No. 13/171,151 dated Dec. 24, 2013, 8 pages.

International Preliminary Report on Patentability in Related Application PCT/US2011/067741, dated Jan. 16, 2014, 12 pages.

Response to Final Office Action in related U.S. Appl. No. 12/886,971 dated Dec. 30, 2013, 12 pages.

Final Office Action in related U.S. Appl. No. 12/886,971 dated Aug. 29, 2013, 10 pages.

Non Final Office Action in related U.S. Appl. 12/886,971 dated Mar. 13, 2013, 11 pages.

International Search Report and Written Opinion from related PCT Application PCT/US2019/048804 dated Jan. 28, 2020, 20 pages.

Invitation to Pay Additional Fees and, Where Applicable, Protest Fee from related PCT Application PCT/US2019/048804 dated Nov. 29, 2019, 14 pages.

* cited by examiner

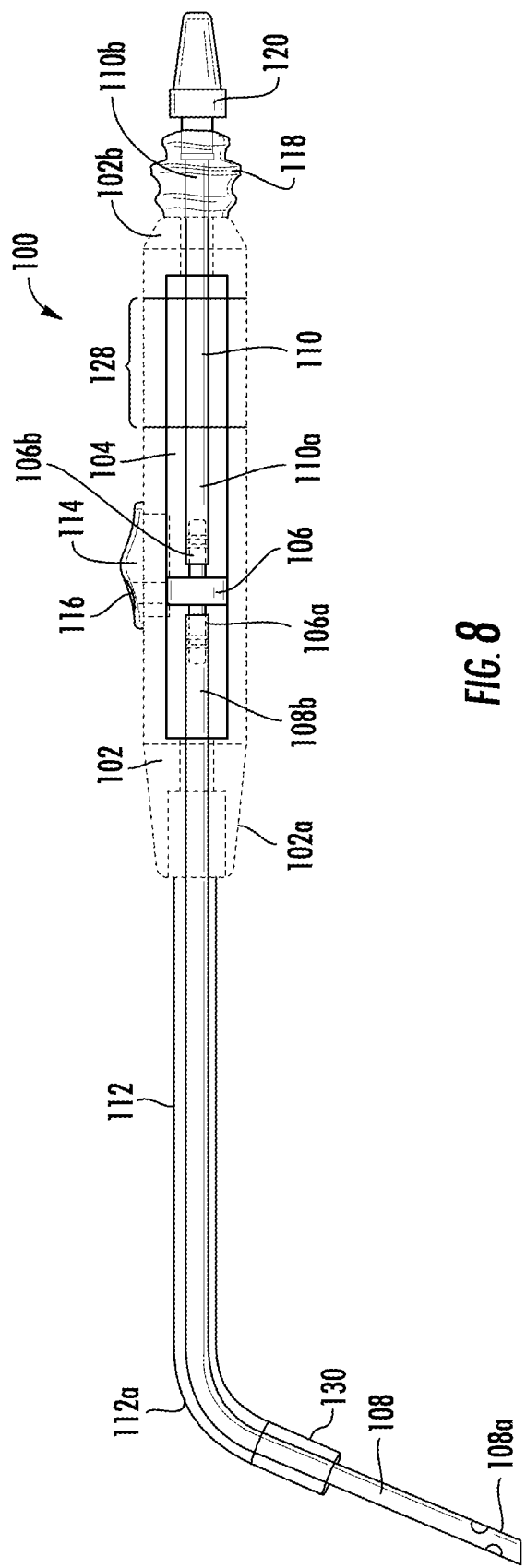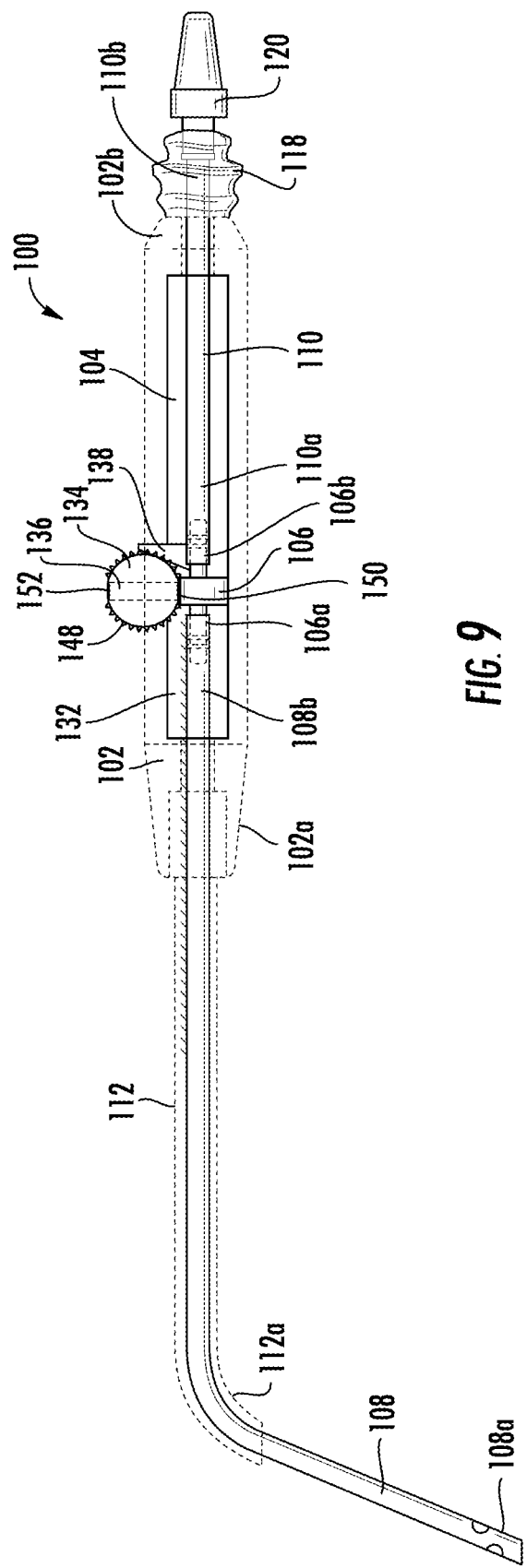

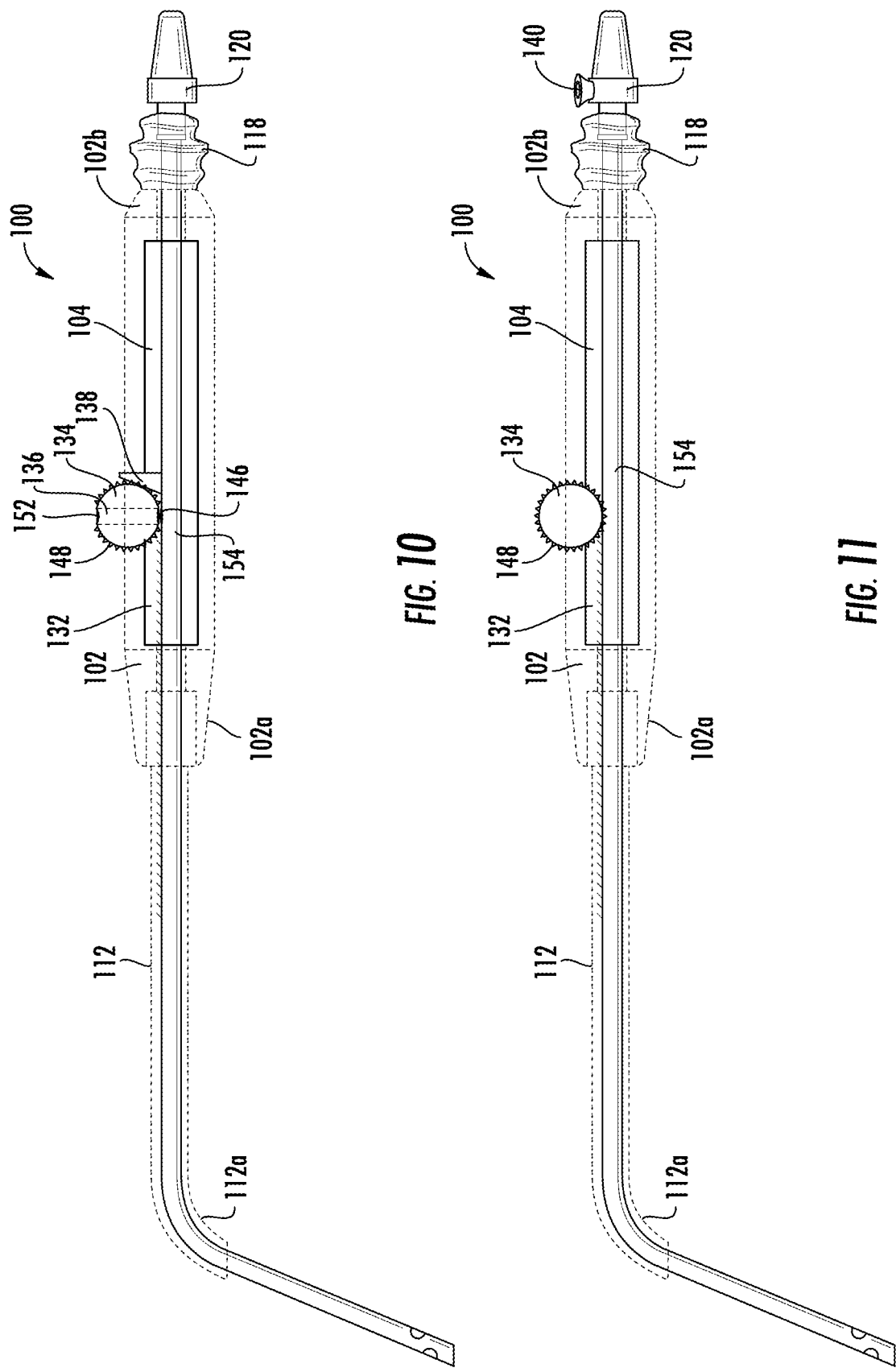

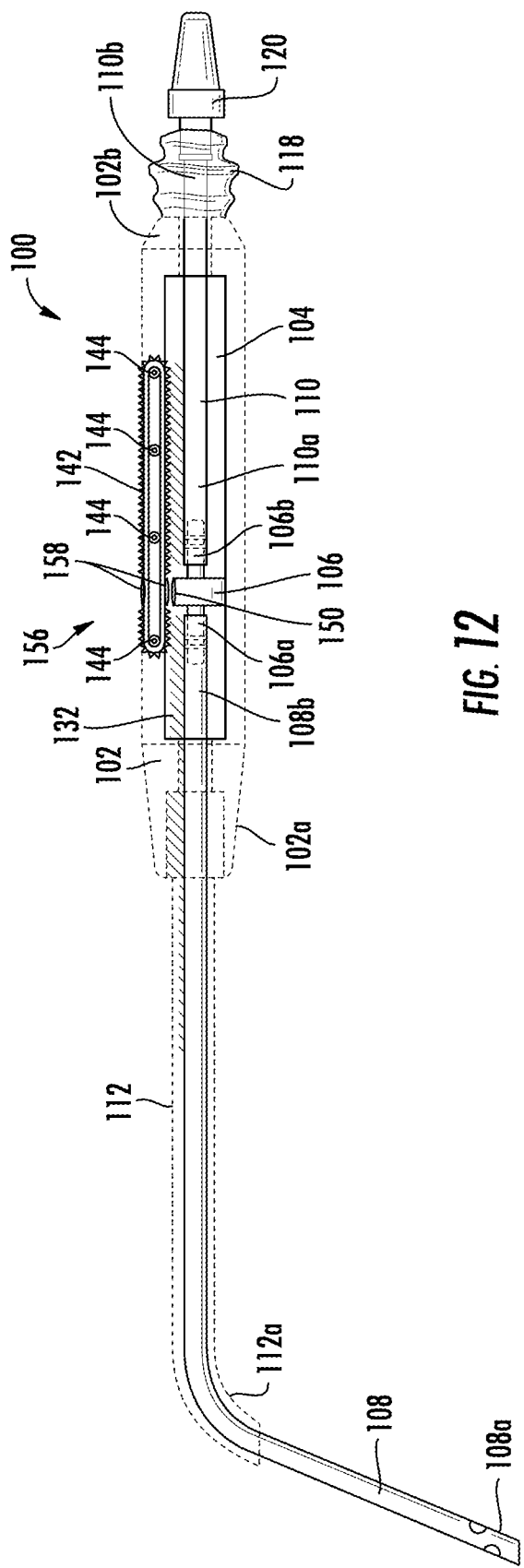
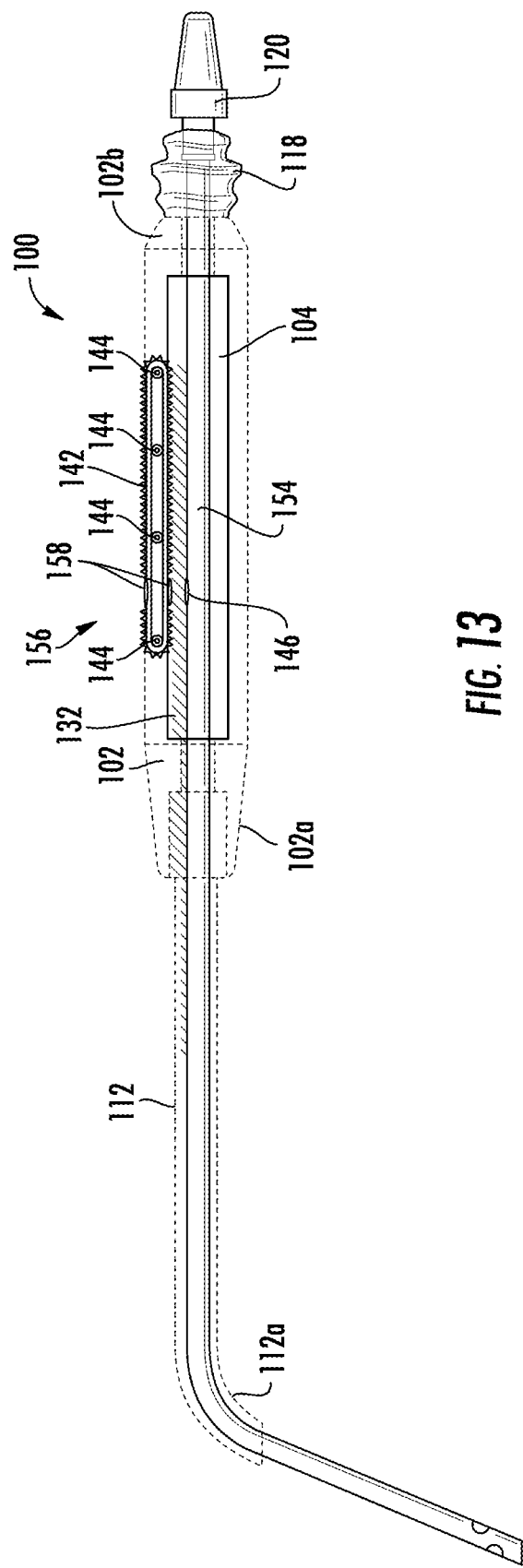

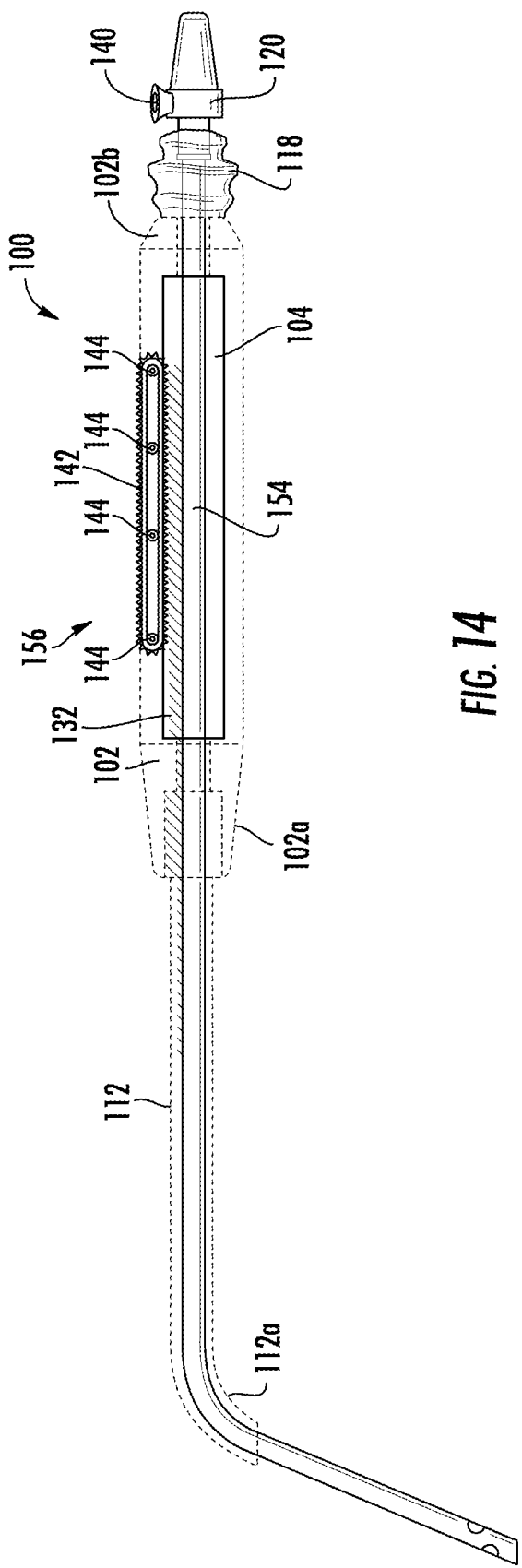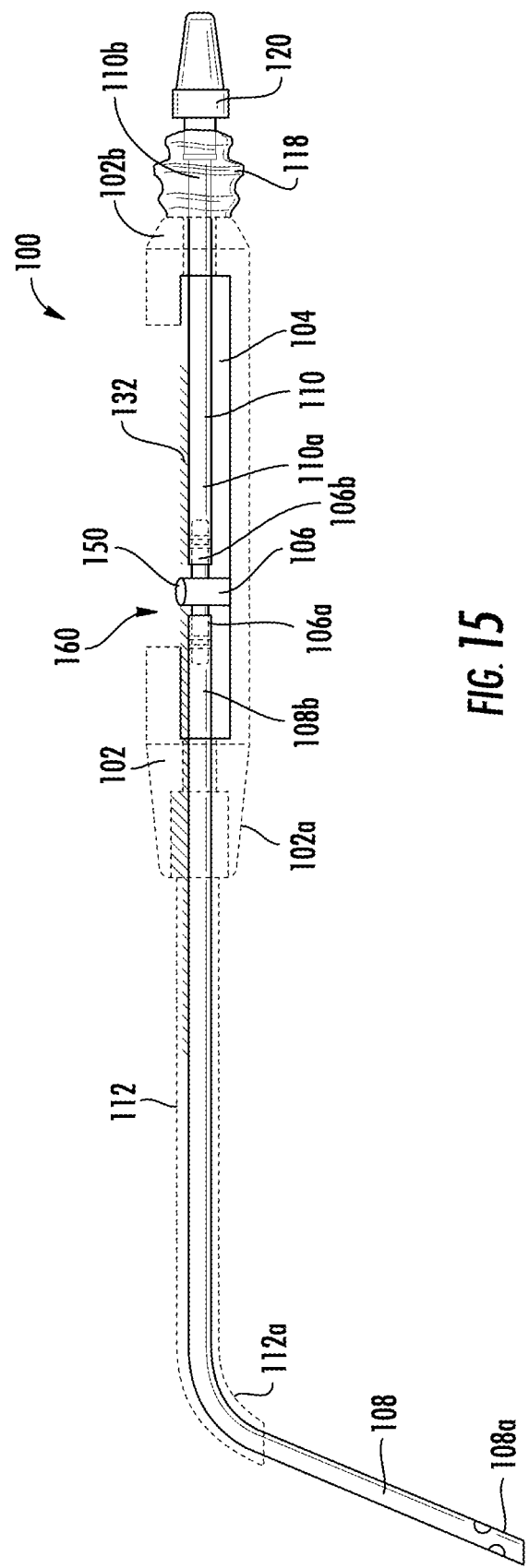

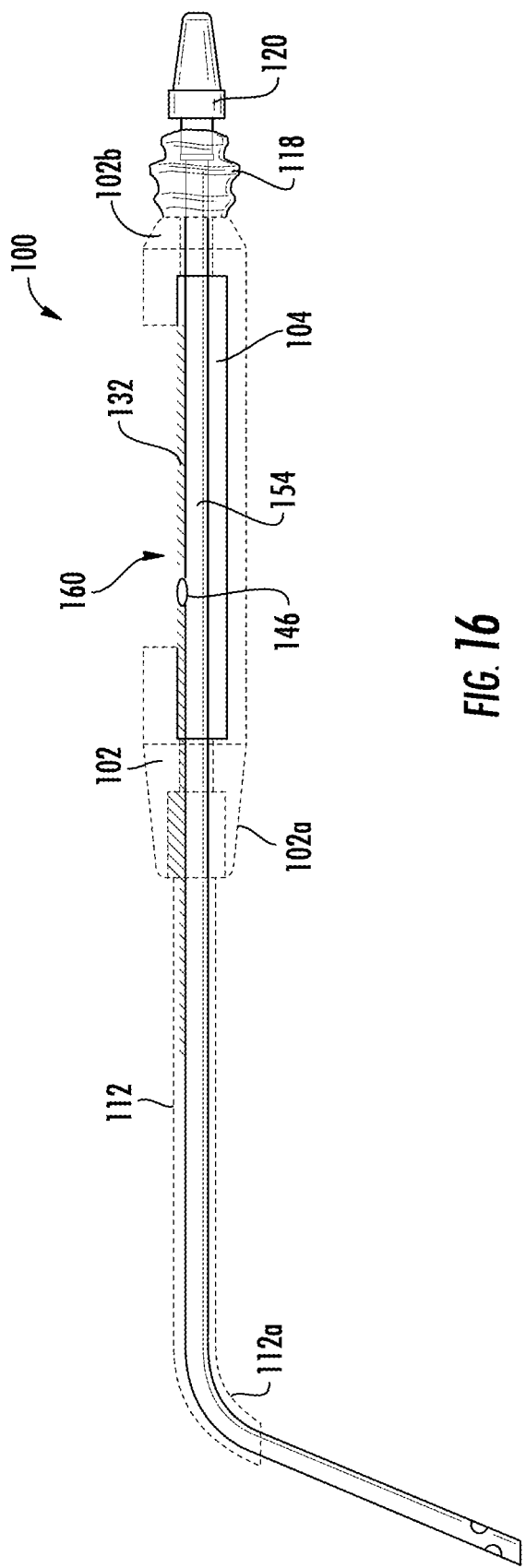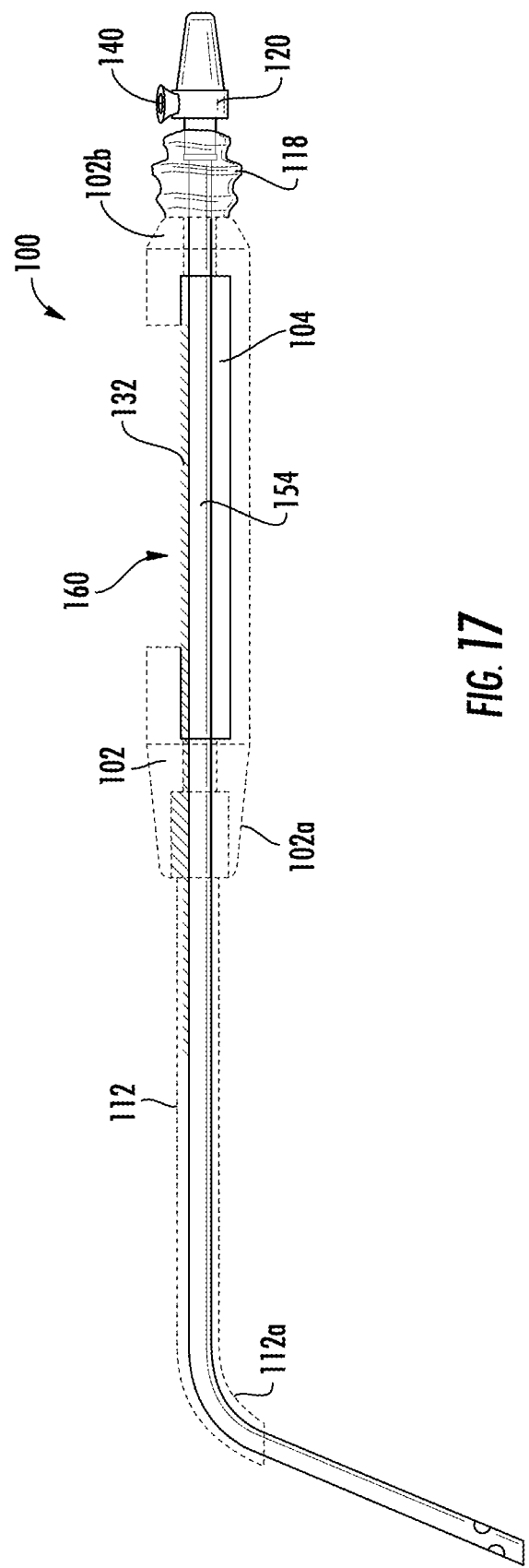

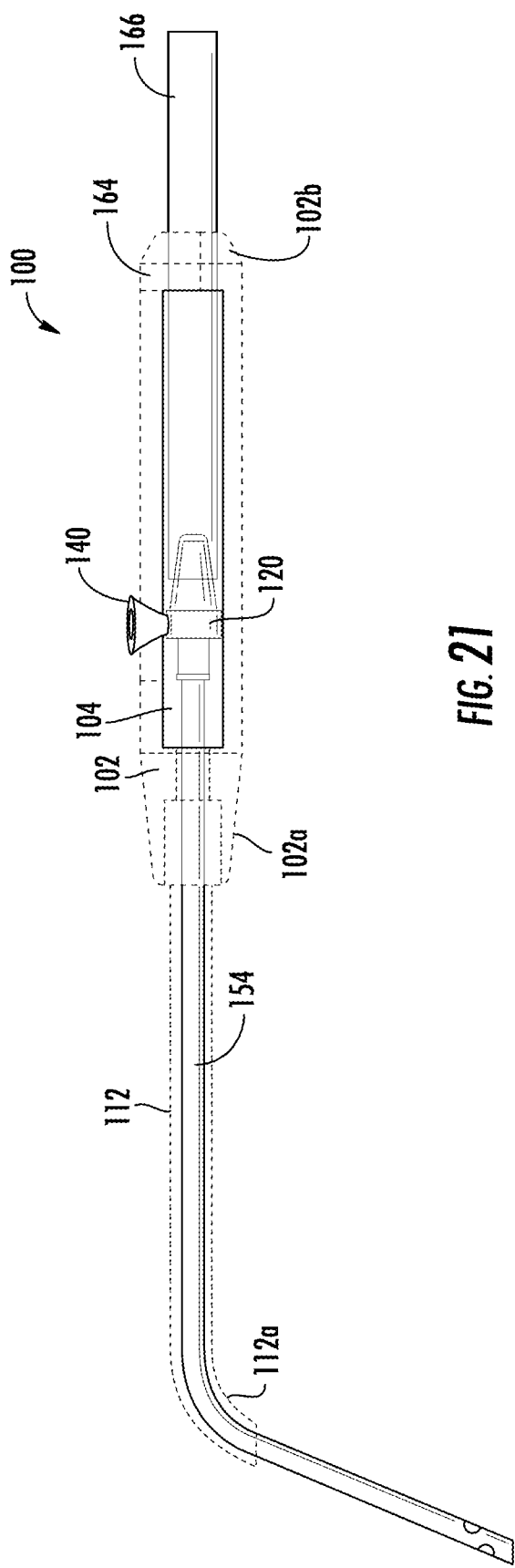
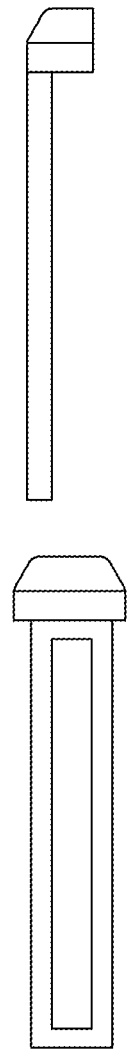
FIG. 21
FIG. 21A  FIG. 21B

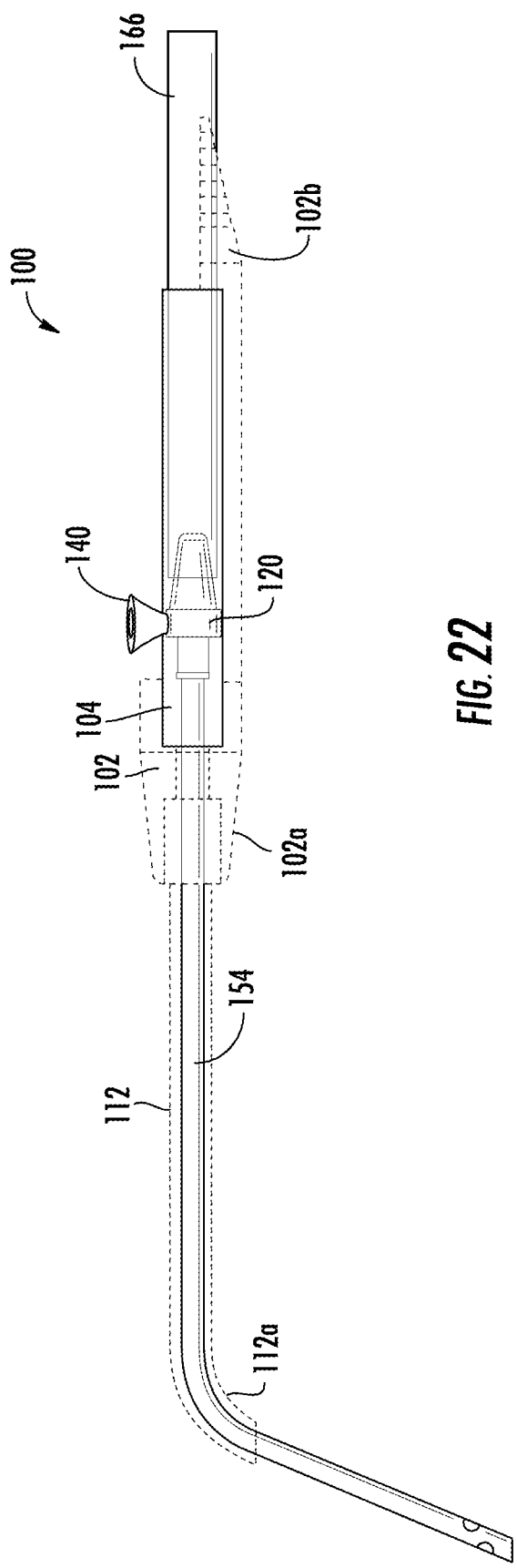
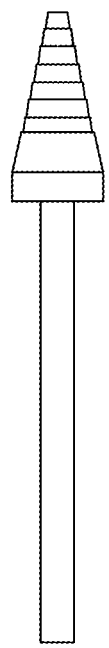
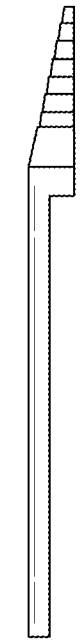
FIG. 22
FIG. 22A
FIG. 22B

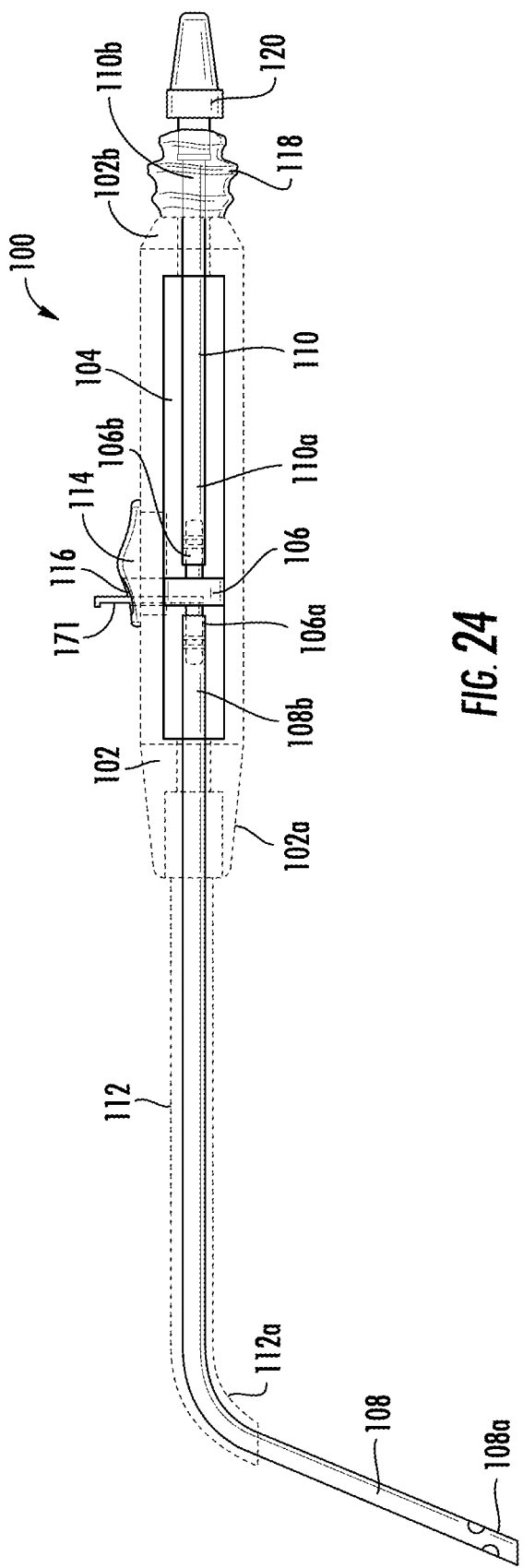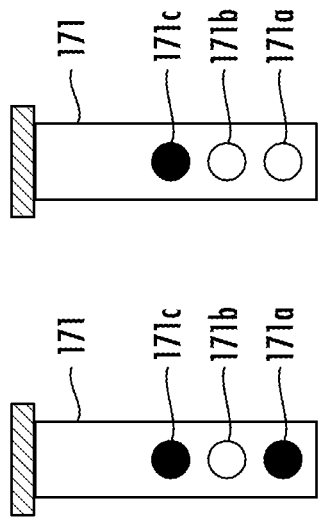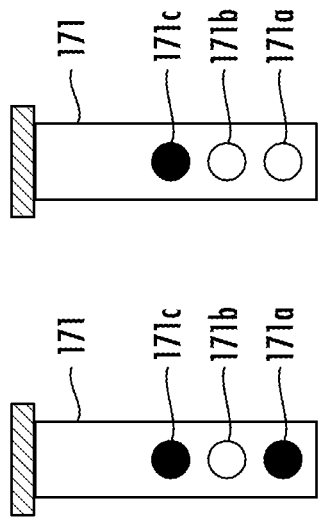

TRACHEAL AND PHARYNGEAL SUCTION DEVICE

FIELD OF THE INVENTION

The invention relates to a method, apparatus, and system for performing oral cleaning and suctioning, oropharyngeal suctioning, and orotracheal suctioning.

BACKGROUND

Oral cleaning instruments, oral suctioning instruments, and suction catheters are commonly used in health care patients with respiratory distress, critical illness, chronic illness, terminal illness, weakness, paralysis, or any patient requiring breathing support from a ventilator.

To perform oral cleaning, most caregivers use foam swabs with various antiseptic solutions to clean and moisten a patient's mouth. Oral suctioning is commonly performed by inserting a rigid plastic tube, often called a Yankauer suction, into a patient's mouth to suction out saliva and mucus. The purpose of oral cleaning and oral suctioning is to remove bacteria that build up in the mouth of patients who are unable to perform oral care, such as brushing their teeth. Various studies have shown that the buildup of bacteria in patients who are unable to perform oral care increases their risk of the nosocomial pneumonias, hospital acquired pneumonia ("HAP") and ventilator associated pneumonia ("VAP"), due to the aspiration of saliva and secretions with high levels of bacteria.

Tracheal and pharyngeal suctioning is commonly performed to suction out secretions when a non-intubated patient is too weak to cough up secretions on their own. Sometimes pharyngeal suctioning is performed in an intubated or tracheostomy patient to reach secretions that have passed down to the tracheal and pharyngeal area. Tracheal and pharyngeal suctioning may be performed via either nasal route suctioning or oral route suctioning. In either case, a tracheal suction catheter is used, which typically is a soft, pliable plastic or rubber tube. In the case of nasotracheal suctioning, the tracheal suction catheter is inserted into the naris and continues down the trachea. Once the tracheal suction catheter reaches the trachea, the unwanted secretions are suctioned out. The nasotracheal or nasopharyngeal suctioning method can cause nasal trauma, pain, and bleeding. In addition, the suction catheter also has a tendency to coil in the back of the throat and may trigger the patient's gag reflex.

Typically, orotracheal or oropharyngeal suctioning is attempted in patients with increased coagulation times, nasal fracture, deviated septum, or if coiling continues to occur in the nasotracheal approach. To perform orotracheal suctioning, the tracheal suction catheter is inserted into the mouth and continues down the trachea. Once the tracheal suction catheter reaches the trachea, the unwanted secretions are suctioned out. Similar to the nasotracheal suctioning method, the suction catheter has a tendency to coil in the back of the throat and may trigger the patient's gag reflex.

Patients are usually in an altered mental state from sedation, confusion, or being frightened and sometimes do not cooperate for oral cleaning, oral suctioning, and tracheal and pharyngeal suctioning. Patients sometimes bite down on the cleaning and suctioning instruments, which can stop the oral cleaning, oral suctioning, and tracheal and pharyngeal suctioning processes, and sometimes break a piece of the instrument off in the patient's mouth or even bite caregivers' fingers. Other problems that exist include instrument insertion trauma to the nose or mouth and the spread of bacteria from the mouth to the lungs during tracheal suctioning.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a tracheal and pharyngeal suction device comprises a handle comprising an interior cavity within the handle; a connector positioned within the interior cavity and moveable along at least a portion of a length of the interior cavity between a retracted position and an extended position; a proximal suction catheter having a coupling portion and a treatment portion, wherein the coupling portion is coupled to a proximal side of the connector; and a distal suction catheter coupled to a distal side of the connector; wherein the treatment portion of the proximal suction catheter extends beyond a proximal end of the handle when the connector is in the extended position.

In some embodiments, the treatment portion of the proximal suction catheter is positioned within at least one of a tracheal region and a pharyngeal region of a patient's throat when the handle is positioned within a patient's mouth and the connector is in the extended position.

In certain embodiments, the connector travels a distance ranging from 0.25 inches to 10 inches between the retracted position and the extended position.

The handle, in some embodiments, further comprises an oral suction tube coupled to the proximal end of the handle, wherein at least the coupling portion of the proximal suction catheter is positioned within the oral suction tube.

In certain embodiments, the treatment portion of the proximal suction catheter is retracted within the oral suction tube when the connector is in the retracted position.

In some embodiments, the treatment portion of the proximal suction catheter extends a distance ranging from 0.25 inches to 10 inches outside of the oral suction tube when the connector is in the extended position.

The handle, in certain embodiments, further comprises an actuator positioned along an outer surface of the handle and configured to cause the connector to translate between the retracted position and the extended position.

A duct, in some embodiments, extends between the interior cavity and the atmosphere surrounding the handle.

In certain embodiments, a duct extends between the connector and the atmosphere surrounding the handle.

In some embodiments, the duct is uncovered when the connector is transitioned from the retracted position to the extended position and is covered when the connector is transitioned from the extended position to the retracted position.

When the distal suction catheter is coupled to a vacuum source, in certain embodiments, the duct diverts suction away from the proximal suction catheter when the duct is uncovered and applies suction to the proximal suction catheter when the duct is covered.

The handle, in some embodiments, comprises an adjustable stop configured to adjust a location of the extended position by preventing the connector from traveling beyond the location of the adjustable stop in a proximal direction of the handle.

In certain embodiments, the proximal suction catheter is detachable from the connector of the handle.

In some embodiments, the handle comprises multiple separable components, wherein an extender is positioned between the multiple separable components.

The oral suction tube, in certain embodiments, comprises a guard coupled to an outer surface of the oral suction tube.

According to certain embodiments of the present invention, a method of using a tracheal and pharyngeal suction device that comprises a handle; a connector moveable along at least a portion of a length of an interior cavity in the handle; a duct; a proximal suction catheter having a treatment portion; and a distal suction catheter, comprises inserting the handle into a patient's mouth; extending at least the treatment portion of the proximal suction catheter beyond a proximal end of the handle to a desired distance within a patient's throat; covering the duct to engage suction through the proximal suction catheter; and retracting at least the treatment portion of the proximal suction catheter.

In some embodiments, the method comprises measuring the patient's throat to find the desired distance.

In certain embodiments, the method comprises attaching an adjustable stop to prevent the connector from traveling beyond a location of the adjustable stop in a proximal direction of the handle.

In some embodiments, the method comprises retracting at least the treatment portion of the proximal suction catheter as a user removes the handle from the patient's mouth.

According to certain embodiments of the present invention, a tracheal and pharyngeal suction system comprises a tracheal and pharyngeal suction device comprising: a handle comprising an interior cavity within the handle; a connector positioned within the interior cavity and moveable along at least a portion of a length of the interior cavity between a retracted position and an extended position; a proximal suction catheter having a coupling portion and a treatment portion, wherein the coupling portion is coupled to a proximal side of the connector; and a distal suction catheter coupled to a distal side of the connector; an oral suction tube coupled to a proximal end of the handle; an actuator positioned along an outer surface of the handle and coupled to the connector, wherein the actuator comprises an duct; an adjustable stop configured to adjust a location of the extended position by preventing the actuator from traveling beyond the location of the adjustable stop in a proximal direction of the handle; a port coupled to the distal suction catheter; a covering coupled to a distal end of the handle and to the port; a guard which may be attached to the oral suction tube to prevent the handle from being inserted too far into a patient's mouth; a measurement device; and an extender which may be attached to the handle to allow for the proximal suction catheter to be extended different lengths.

According to certain embodiments of the present invention a tracheal and pharyngeal suction device comprises a handle comprising an interior cavity within the handle; a main suction catheter extending a length of the tracheal and pharyngeal suction device, wherein the main suction catheter is a single continuous length; and a port coupled to the main suction catheter.

In some embodiments, the tracheal and pharyngeal suction device further comprises an opening located on at least one of the main suction catheter or the port.

BRIEF DESCRIPTION OF THE DRAWINGS

FIG. 8 is a side view of the tracheal and pharyngeal suction device of FIG. 1 with an oral suction tube extender and a handle extender.

FIG. 9 is a side view of the tracheal and pharyngeal suction device of FIG. 1 with a spinning wheel actuator.

FIG. 10 is a side view of the tracheal and pharyngeal suction device of FIG. 9 without a connector.

FIG. 11 is a side view of the tracheal and pharyngeal suction device of FIG. 9 without a connector and with a thumb port opening.

FIG. 12 is a side view of the tracheal and pharyngeal device of FIG. 1 with a continuous track actuator.

FIG. 13 is a side view of the tracheal and pharyngeal suction device of FIG. 12 without a connector FIG. 14 is a side view of the tracheal and pharyngeal suction device of FIG. 12 without a connector and with a thumb port opening.

FIG. 15 is a side view of the tracheal and pharyngeal suction device of FIG. 1 with an open handle.

FIG. 16 is a side view of the tracheal and pharyngeal suction device of FIG. 15 without a connector.

FIG. 17 is another side view of the tracheal and pharyngeal suction device of FIG. 15 without a connector and with a thumb port opening.

FIG. 21 is a side view of the tracheal and pharyngeal suction device of FIG. 20 without an actuator and with a snap fit back piece.

FIG. 21A is a top view of the snap fit back piece of FIG. 21.

FIG. 21B is a side view of the snap fit back piece of FIG. 21.

FIG. 22 is a side view of a further embodiment of the tracheal and pharyngeal suction device of FIG. 21.

FIG. 22A is a top view of a snap fit back piece of FIG. 22.

FIG. 22B is a side view of a snap fit back piece of FIG. 22.

FIG. 24 is a side view of the tracheal and pharyngeal suction device of FIG. 1 with a sliding member.

FIGS. 24 A and B are front views of the sliding member of FIG. 24.

DETAILED DESCRIPTION

Figure 1:
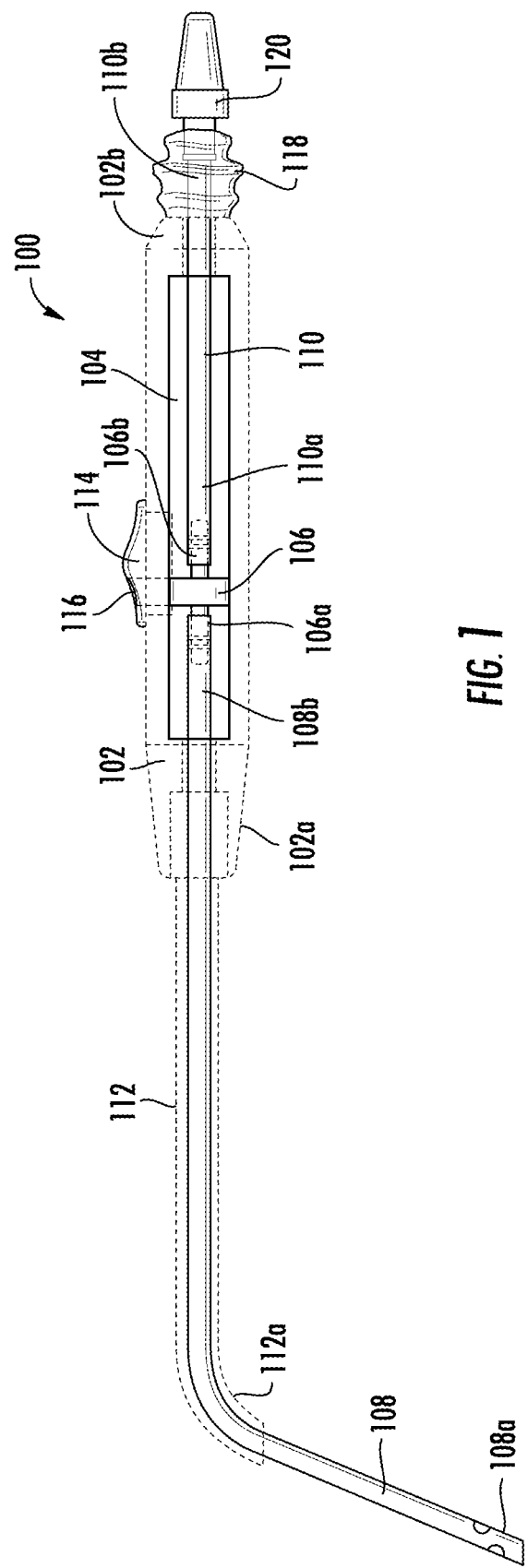
FIG. 1 is a side view of a tracheal and pharyngeal suction device in an extended position, according to certain embodiments of the present invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

FIGS. 1-26 illustrate certain embodiments of a tracheal and pharyngeal suction device 100. In some of these embodiments, the tracheal and pharyngeal suction device 100 comprises a handle 102, a connector 106, a proximal suction catheter 108, and a distal suction catheter 110. In further embodiments, the tracheal and pharyngeal suction device 100 may comprise a handle 102 and a main suction catheter 154.

In some embodiments, the handle 102 may be constructed of a rigid material, such as plastic, steel, or any other suitable material. The handle 102 may have a circular cross-section or other suitable cross-sectional shape including but not limited to rectilinear, oval, crescent, triangular, pentagonal, hexagonal, octagonal, D-shaped, and I-shaped. However, one of skill in the relevant art will understand that the handle 102 may have any appropriate shape that allows a user to use the tracheal and pharyngeal suction device 100 to accomplish the desired task while minimizing potential injury to the patient or the user. In some embodiments, the handle 102 may include a textured surface to prevent the tracheal and pharyngeal suction device 100 from slipping during use. In further embodiments, the handle 102 may include indentations for the user's fingers when the handle 102 is grasped. In still further embodiments, the handle 102 is configured to enter a patient's mouth cavity without entering the patient's throat.

Figure 2:
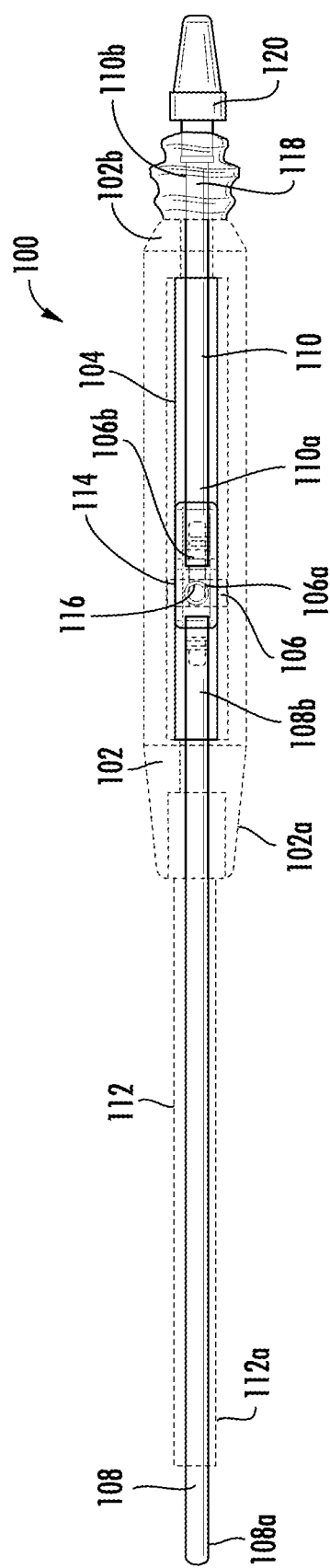
FIG. 2 is a top view of the tracheal and pharyngeal suction device of FIG. 1.
Figure 3:
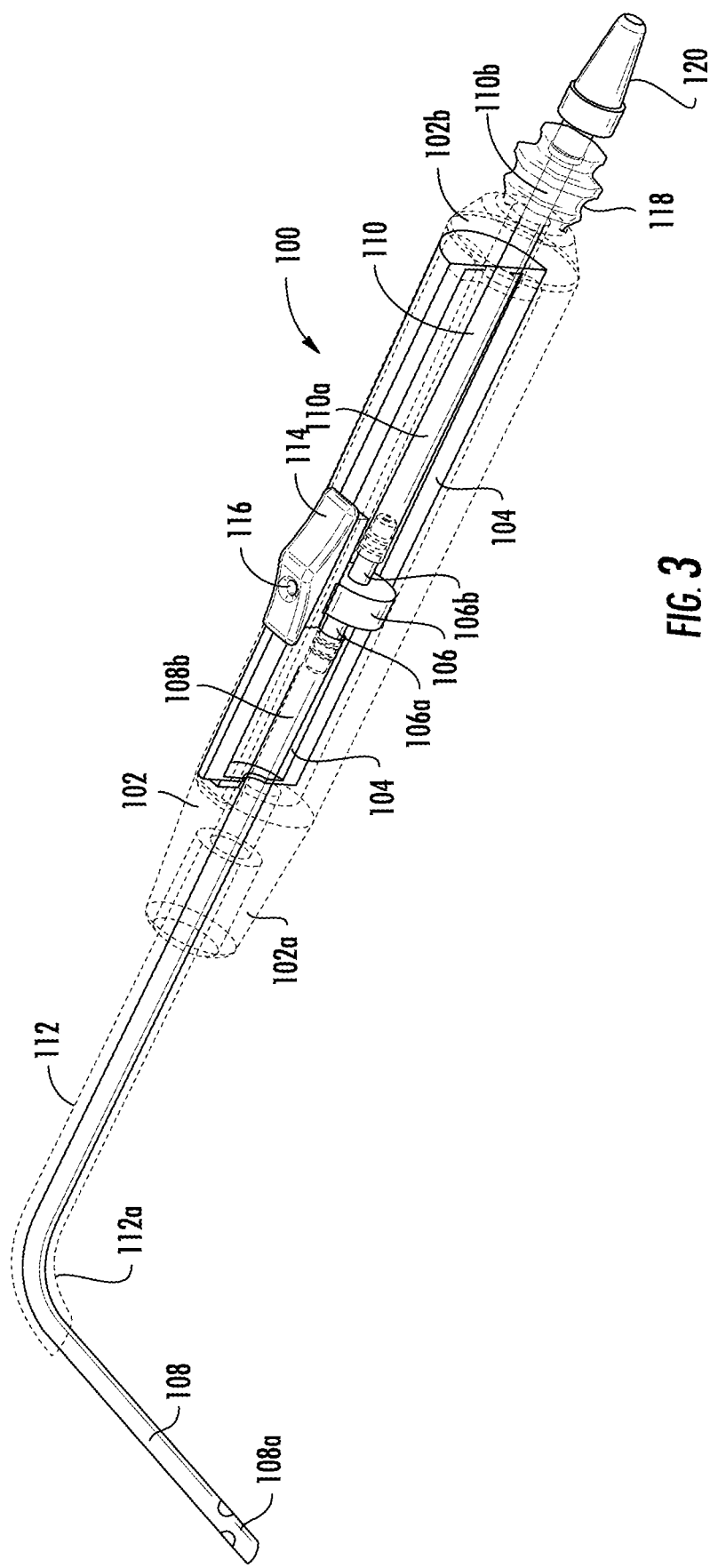
FIG. 3 is a top perspective view of the tracheal and pharyngeal suction device of FIG. 1.

In some embodiments, the handle 102 may include an interior cavity 104 within and extending the length of the handle 102, as best illustrated in FIGS. 1-3. In further embodiments, the handle 102 may include an opening 160 into the interior cavity 104, as best illustrated in FIGS. 15-17, and as described in more detail below. The connector 106 may have extrusions extending from a proximal end 106a and/or a distal end 106b of the connector 106. The proximal end 106a of the connector 106 is the end that is closest to the patient when the tracheal and pharyngeal suction device 100 is in use. In contrast, the distal end 106b of the connector 106 is the end that is closest to the user when the tracheal and pharyngeal suction device 100 is in use.

Figure 4A:
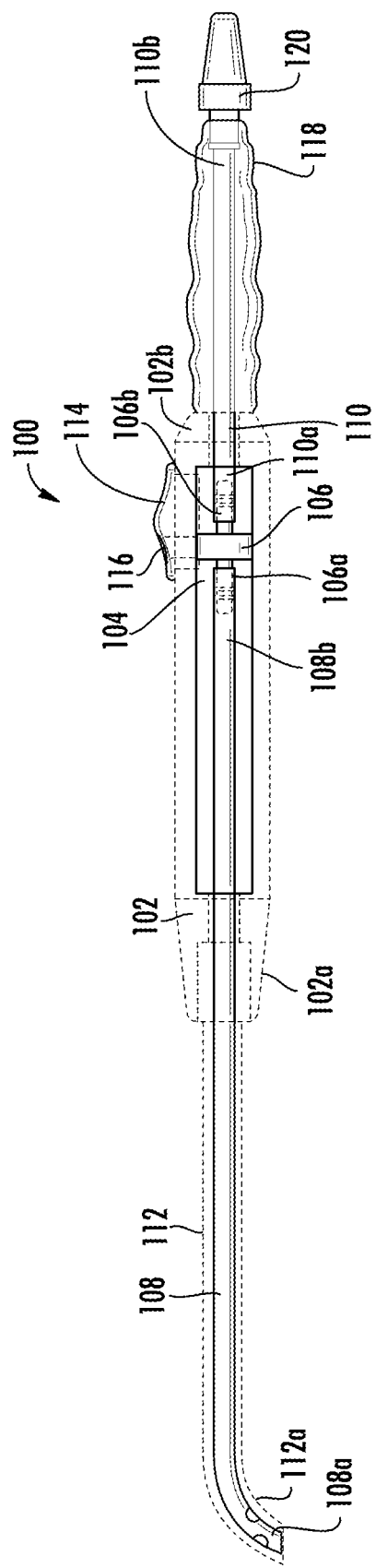
FIG. 4A is a side view of the tracheal and pharyngeal suction device of FIG. 1 in a retracted position.
Figure 4:
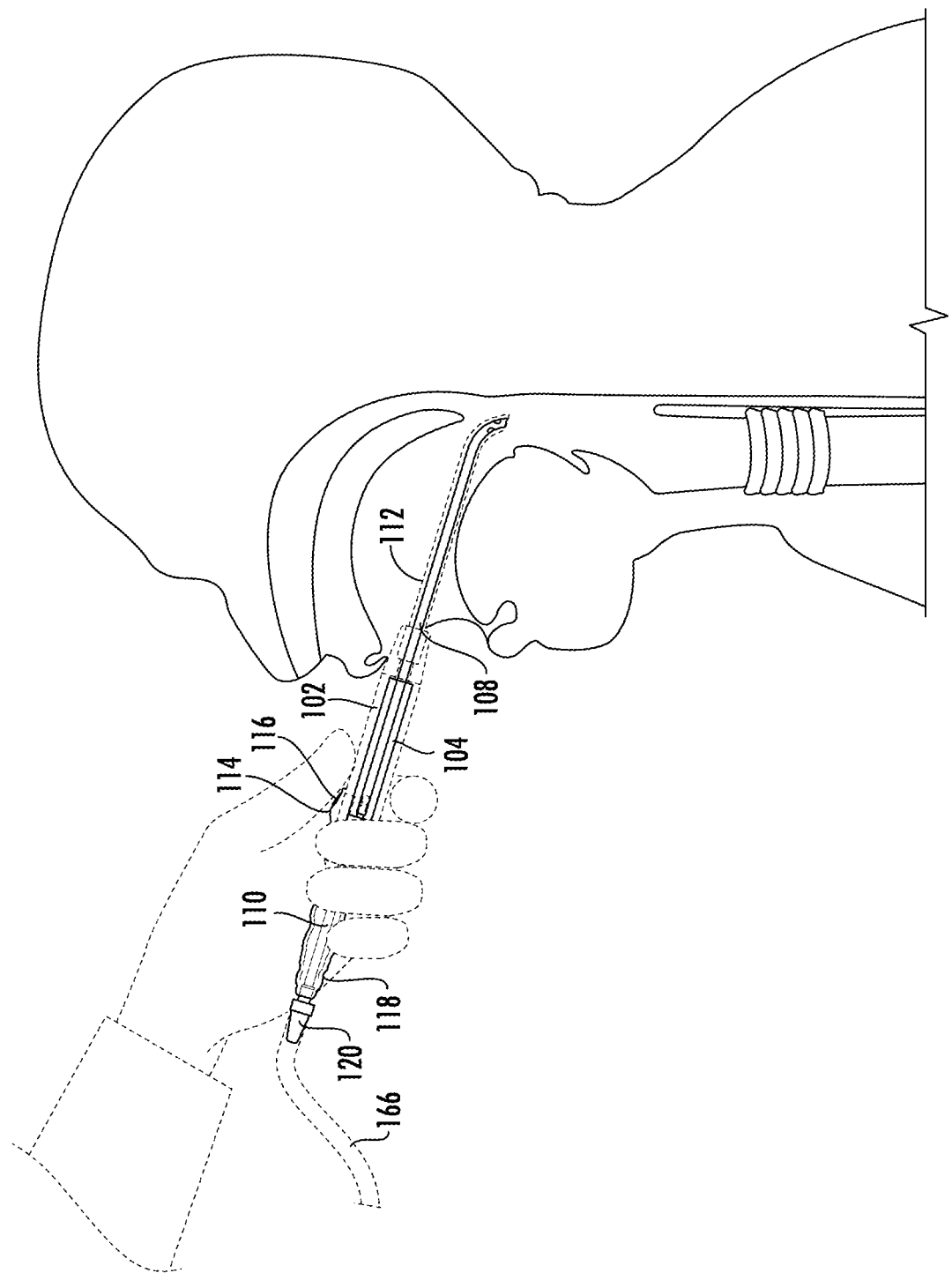
FIG. 4 is a side view of the tracheal and pharyngeal suction device of FIG. 1 in a retracted position in use during an oral suctioning procedure.
Figure 5:
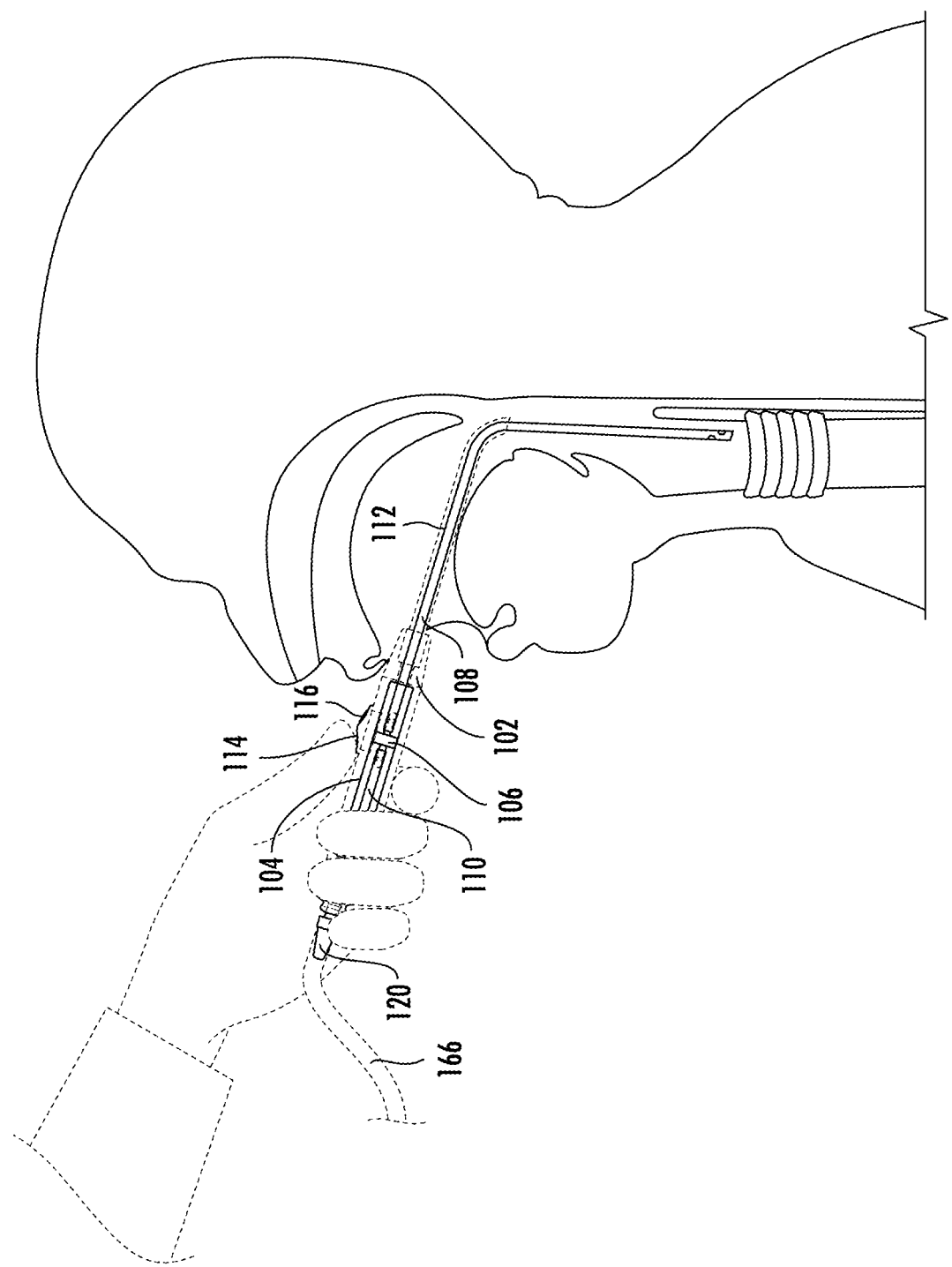
FIG. 5 is another side view of the tracheal and pharyngeal suction device of FIG. 1 in an extended position in use during an oral suctioning procedure.
Figure 23:
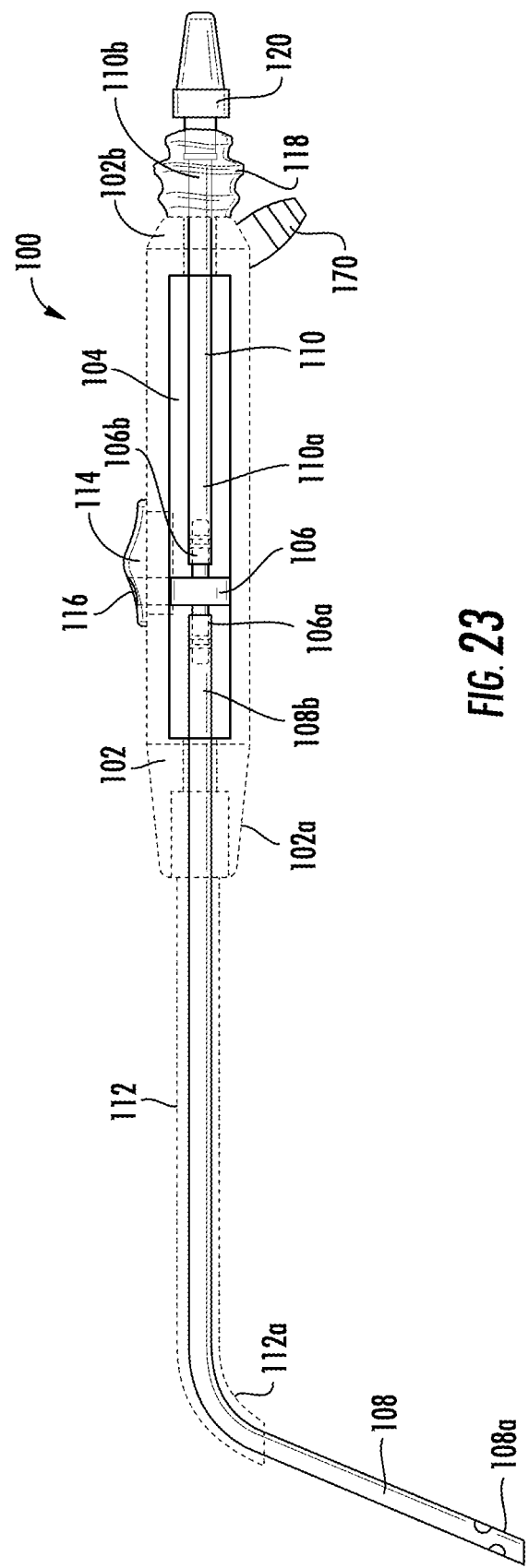
FIG. 23 is a side view of the tracheal and pharyngeal suction device of FIG. 1 with a suction port.

The connector 106 may be positioned within the interior cavity 104 and moveable along at least a portion of the length of the interior cavity 104 between a retracted position (as best shown in FIGS. 4A and 4) and an extended position (as best shown in FIGS. 1 and 5). In some embodiments, the connector 106 may be constructed of the same rigid material, such as plastic, steel, or any other suitable material, that is used to construct the handle 102. However, one of skill in the relevant art will understand that the handle 102 and the connector 106 are not required to be made of the same material. In some embodiments, the handle 102 may include a suction port 170, as best illustrated in FIG. 23, located on the proximal side or distal side of the handle 102. The suction port 170 may connect to a collection container and a device that generates suction (not shown) and allows a user to sterilize the interior cavity 104 between applications or uses of the tracheal and pharyngeal suction device 100.

As best illustrated in FIGS. 4A and 4, the connector 106 is in the retracted position when the connector 106 is positioned closer to a distal end 102b of the handle 102. The distal end 102b of the handle 102 is the end that is closest to the user when the tracheal and pharyngeal suction device 100 is in use.

In contrast, as best illustrated in FIGS. 1 and 5, the connector 106 is in the extended position when the connector 106 is positioned closer to a proximal end 102a of the handle 102. The proximal end 102a of the handle 102 is the end that is closest to the patient when the tracheal and pharyngeal suction device 100 is in use.

In some embodiments, the connector 106 travels at least 7.62 centimeters (3 inches) between the retracted position and the extended position. In further embodiments, the connector travels a distance that may range from 0.635 centimeters (0.25 inches) to 25.4 centimeters (10 inches) between the retracted position and the extended position. In still further embodiments, the connector 106 travels a distance that is suitable for the patient. For example, if the tracheal and pharyngeal suction device 100 is used on a child, the connector may travel a smaller distance than 7.62 centimeters (3 inches) whereas if the tracheal and pharyngeal suction device 100 is used on a tall patient, the connector may travel a greater distance than 7.62 centimeters (3 inches).

Figure 7:
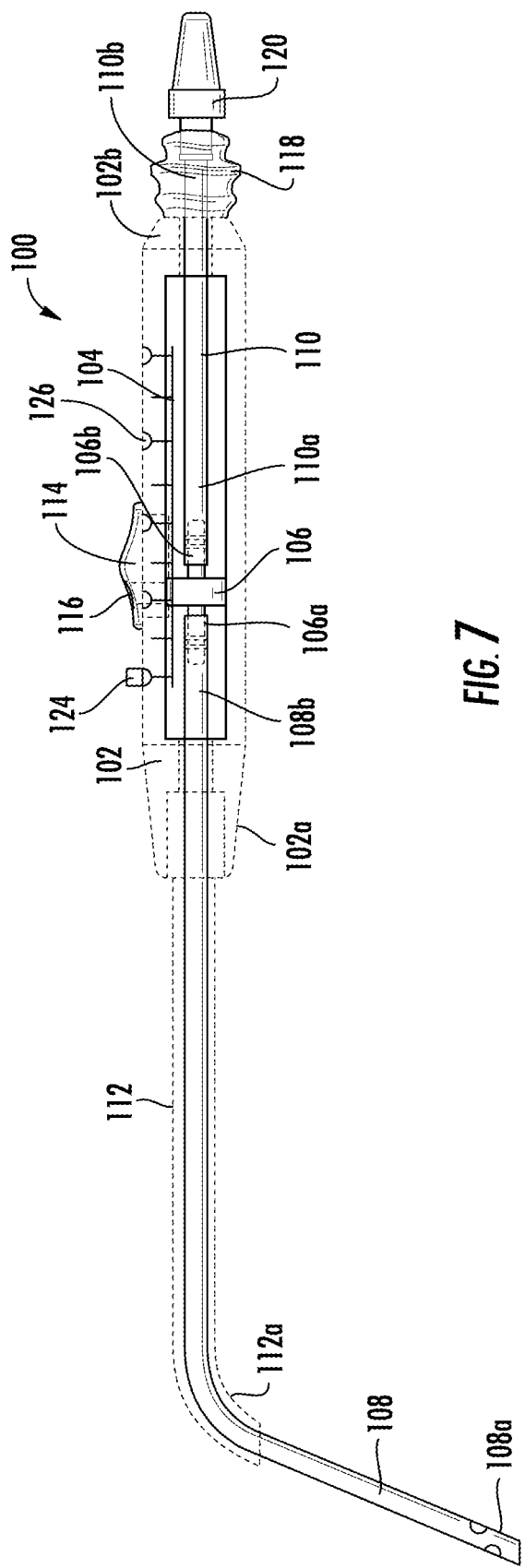
FIG. 7 is a side view of the tracheal and pharyngeal suction device of FIG. 1 with an adjustable stop.

In some embodiments, as best illustrated in FIG. 7, the handle 102 may have markings on the outer surface of the handle 102 that enable the user to measure the distance the connector 106 has travelled. In some embodiments, the markings on the outer surface of the handle 102 may be used to measure the throat of the patient so the user will know how far the connector 106 will need to travel. In further embodiments, the outer surface of the handle 102 may have two sets of markings. One set may be used to measure the distance the connector 106 has travelled and the other set may be used to measure the throat of the patient so the user will know how far the connector 106 will need to travel. In still further embodiments, the tracheal and pharyngeal suction device 100 may come with a separate device (not shown) that is capable of measuring the distance the connector 106 has travelled and the throat of the patient so the user will know how far the connector 106 will need to travel.

The proximal suction catheter 108 may have a treatment portion 108a and coupling portion 108b. The coupling portion 108b is coupled to the proximal end 106a of the connector 106. In some embodiments, the coupling portion 108b is coupled to the extrusion located on the proximal end 106a of the connector 106. However, a person of ordinary skill in the relevant art would understand that the coupling portion 108b may be coupled in any suitable manner and in any suitable location. The treatment portion 108a extends beyond the proximal end 102a of the handle 102 when the connector 106 is in the extended position. In some embodiments, the treatment portion 108a is positioned within the tracheal and pharyngeal region of a patient's throat when the handle 102 is positioned within the patient's mouth and the connector 106 is in the extended position. In further embodiments, the proximal suction catheter 108 may be detachable from the connector 106 such that the proximal suction catheter 108 is interchangeable with proximal suction catheters of differing lengths. The distal suction catheter 110 of the tracheal and pharyngeal suction device is coupled to the distal end 106b of the connector 106. In some embodiments, the distal suction catheter 110 is coupled to the extrusion located on the distal end 106b of the connector 106. However, person of ordinary skill in the relevant art would understand that the distal suction catheter 110 may be coupled in any suitable manner and in any suitable location. In some embodiments, the distal suction catheter 110 may be detachable from the connector 106 such that the distal suction catheter 110 is interchangeable with distal suction catheters of differing lengths.

Figure 18:
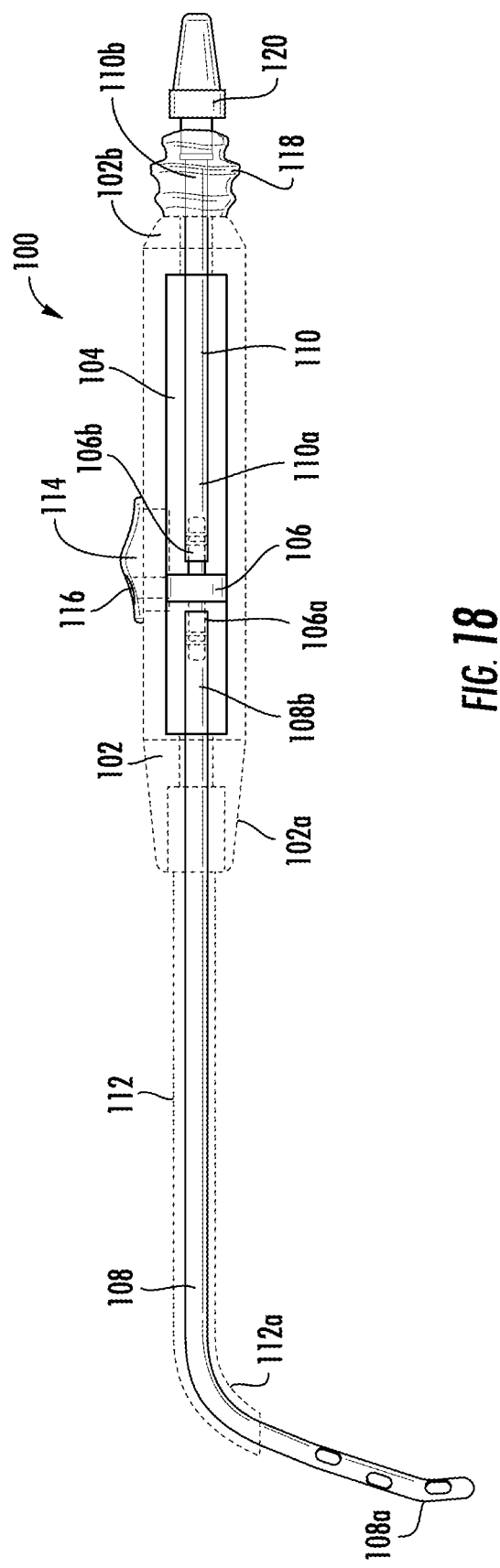
FIG. 18 is a side view of the tracheal and pharyngeal suction device of FIG. 1 with a Coudé tip catheter.

In some embodiments, the proximal suction catheter 108 and the distal suction catheter 110 may comprise a flexible tube of varying lengths made of rubber, plastic, or any other suitable material. In further embodiments, the proximal suction catheter 108 and the distal suction catheter 110 may comprise a Yankauer suction catheter. The proximal suction catheter 108 and the distal suction catheter 110 may range in size from 4 French to 18 French. The French scale is a common unit of measurement for catheters and may be abbreviated as Fr. In some embodiments, the proximal suction catheter 108 and the distal suction catheter 110 are 14 Fr. One of skill in the relevant art will understand that any suitable size of proximal suction catheter 108 and distal suction catheter 110 may be used that will accomplish the desired task while minimizing potential injury to the patient or the user. A straight tip catheter is best illustrated in the embodiments shown in FIGS. 1-17 and 19-23; however, a Coudé tip catheter, as best illustrated in FIG. 18, or any other suitable catheter may be used.

In some embodiments, the distal suction catheter 110 is coupled to a port 120 positioned at a distal end 110b of the distal suction catheter 110. The port 120 may be coupled to a collection container and a device that generates suction. Because the tracheal and pharyngeal suction device 100 is often used with patients that may be particularly susceptible to infection, the distal suction catheter 110 may be enclosed in a covering 118 to prevent the introduction of bacteria into the patient during suctioning. The covering 118 is attached to the distal end 102b of the handle 102 and to the port 120 in order to completely enclose the distal suction catheter 110. In some embodiments, the covering 118 may be a sterile plastic sheath or any other suitable material.

The handle 102 further includes an oral suction tube 112 that is coupled to the proximal end 102a of the handle 102. The oral suction tube 112 may be 15.24 to 17.78 centimeters (6 to 7 inches) long. In some embodiments, at least the coupling portion 108b of the proximal suction catheter 108 is positioned within the oral suction tube 112. When the connector 106 is in the retracted position, the treatment portion 108a of the proximal suction catheter 108 is positioned within the oral suction tube 112. When the connector 106 is in the extended position, the treatment portion 108a of the proximal suction catheter is positioned outside of the oral suction tube 112.

The length and size of various features of the tracheal and pharyngeal suction device 100 including, but not limited to, the handle 102, the interior cavity 104, the connector 106, the proximal suction catheter 108, the distal suction catheter 110, the main suction catheter 154, the oral suction tube 112, and the actuator 114 (which is discussed in detail below) may vary in accordance with the dimensions of the mouth and throat of the patient. For example, the tracheal and pharyngeal suction device 100 may be used with a variety of patients ranging in age from infant to adult and having a range in sizes of mouth and throat cavities. Because the tracheal and pharyngeal suction device 100 may be used with a range of mouth or throat cavities, the tracheal and pharyngeal suction device 100 may be manufactured in a plurality of sizes, wherein each size is configured to fit a particular sized mouth or throat cavity.

In some embodiments, the proximal suction catheter 108, the distal suction catheter 110, and the main suction catheter 154 may be interchangeable with the handle 102 so that the appropriately sized catheters may be used based on the size of the patient. In other embodiments, as best illustrated in FIG. 8, the handle 102 may be detached into two parts and a handle extender 128 may be attached in between the two parts of the handle 102. In certain embodiments, an oral suction tube extender 130 may be attached to a proximal end 112a of the oral suction tube 112. Different oral suction tube extenders 130 may include different angled curves. In some embodiments, the handle extender 128 and the oral suction tube extender 130 may be attached to the handle 102 and oral suction tube 112, respectively, using screws, fasteners, snaps, or any other suitable method of securing the handle extender 128 and the oral suction tube extender 130 to the tracheal and pharyngeal suction device 100. The handle extender 128 and the oral suction tube extender 130 allow the user to adjust the size of the tracheal and pharyngeal suction device 100 so the tracheal and pharyngeal suction device 100 is able to accommodate a variety of sizes of patients.

In some embodiments, the handle 102 may include a detachable piece 164, as best illustrated in FIG. 21. The detachable piece 164 may be removed from handle 102 to permit a main suction catheter 154 of a different length or diameter to be inserted into the tracheal and pharyngeal suction device 100. When the main suction catheter is inserted, the detachable piece 164 may be attached to the handle 102. The detachable piece 164 may be attached to the handle 102 by a snap fit mechanism, a slide and lock mechanism, or any other mechanism suitable for securely attaching the detachable piece 164 to the handle 102. The port 120 attached to the main suction catheter 154 may include a thumb port opening 140. A wall suction tube 166 may be attached to the port 120 and connected to a collection container and a device that generates suction.

Figure 22C:
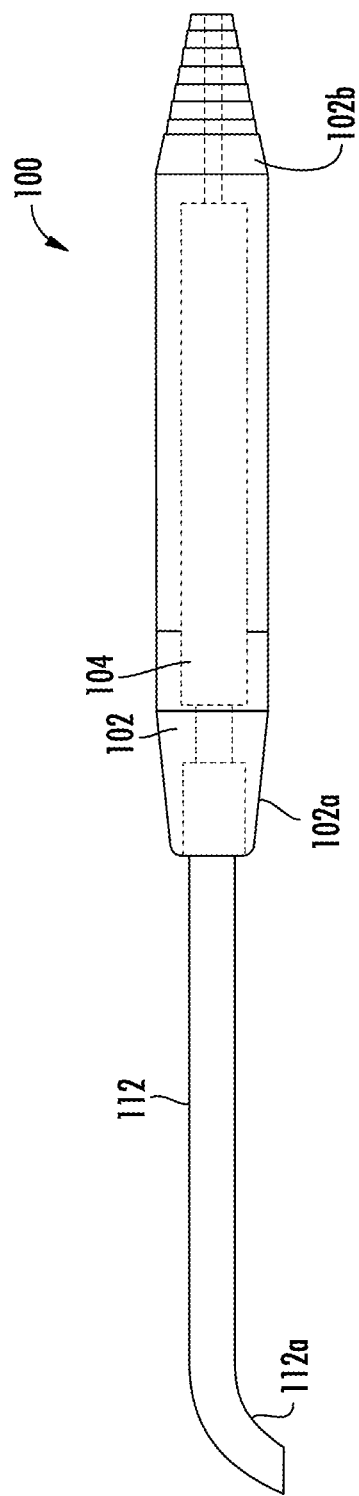
FIG. 22C is a side view of a further embodiment of the tracheal and pharyngeal suction device of FIG. 22 with the snap fit back piece attached.

In further embodiments, the detachable piece 164 and the distal end 102b of the handle 102 may be shaped similar to the shape of the port 120. When the detachable piece 164 is removed from handle 102, the user may extend and retract the main suction catheter 154 using the thumb port opening 140 on the port 120, as best illustrated in FIG. 22. In still further embodiments, the main suction catheter 154 may be removed from the tracheal and pharyngeal suction device 100 and the detachable piece 164 may be attached to the handle 102 so that the wall suction tube 166 may be attached to the distal end 102*b* of the handle 102 and the detachable piece 164. In some embodiments, the oral suction tube 112 may be made of rubber or some other suitable material and may have holes at the proximal end 112*a*.

In some embodiments, the connector 106 may include an actuator 114 that is coupled to the connector 106 and positioned along an outer surface of the handle 102. The actuator 114 may be a thumb switch, a spinning wheel, a continuous track, or any other suitable actuator. A person having ordinary skill in the relevant art will understand that the actuator 114 may be of any design that is capable of causing translational movement of the connector 106, the proximal suction catheter 108, the distal suction catheter 110, or the main suction catheter 154. The connector 106 is hollow with two hollow extrusions where the proximal suction catheter 108 and the distal suction catheter 110 are coupled to the connector 106. In further embodiments, the connector 106 may be hollow with two holes where the proximal suction catheter 108 and the distal suction catheter 110 are coupled to the connector 106. The proximal suction catheter 108 and the distal suction catheter 110 may be coupled to connector 106 using glue, bonding, ultrasonic welding, or any other suitable means of coupling the proximal suction catheter 108 and the distal suction catheter 110 to the connector 106. This allows suction to be applied from the distal suction catheter 110 to the proximal suction catheter 108. In some embodiments, the actuator 114 may include an air duct or vent 116. The air duct 116 serves to divert suction away from the proximal suction catheter 108 when the air duct 116 is uncovered and the distal suction catheter 110 is coupled to a vacuum source by connecting the connector 106 to the atmosphere surrounding the handle 102 and thereby divert suction from the treatment portion 108*a* of the proximal suction catheter 108. When the air duct 116 is covered, either by placing a user's finger over the duct 116 or by some other means, and the distal suction catheter 110 is coupled to a vacuum source, suction is applied to the proximal suction catheter 108. In some embodiments, the air duct 116 is circular. However, it is understood by one of skill in the relevant art that the air duct 116 may be of any shape or size suitable for being covered by a user during use of the tracheal and pharyngeal suction device 100.

Figure 19:
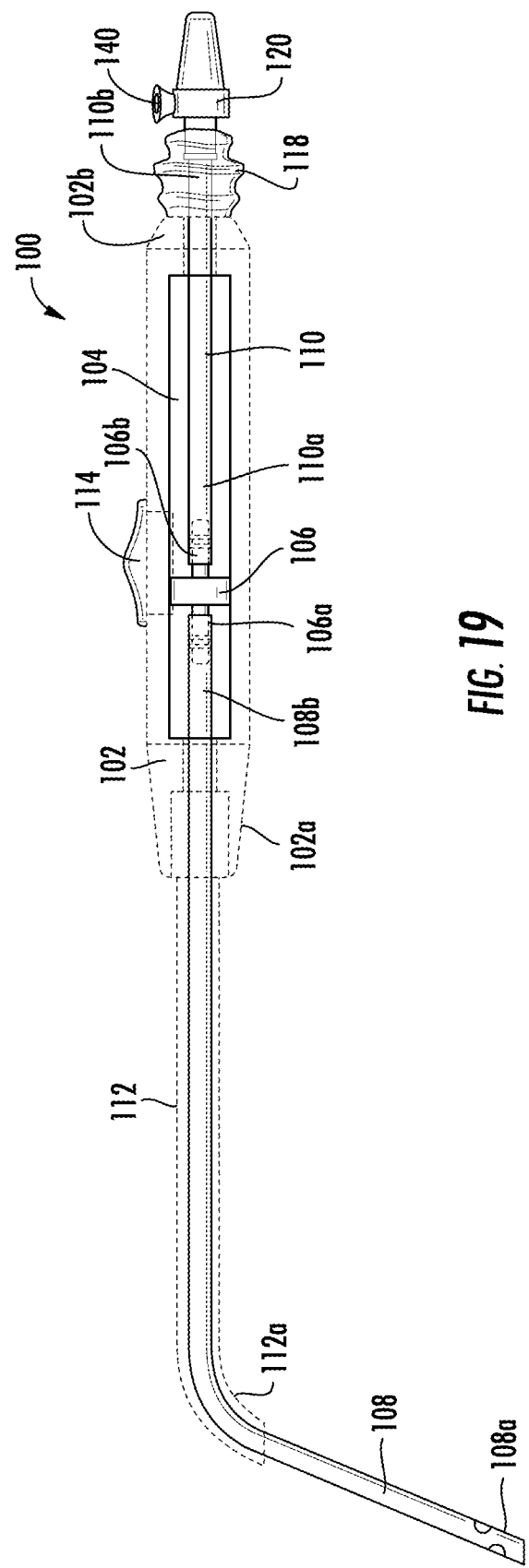
FIG. 19 is a side view of the tracheal and pharyngeal suction device of FIG. 1 with a solid actuator and with a thumb port opening.
Figure 20:
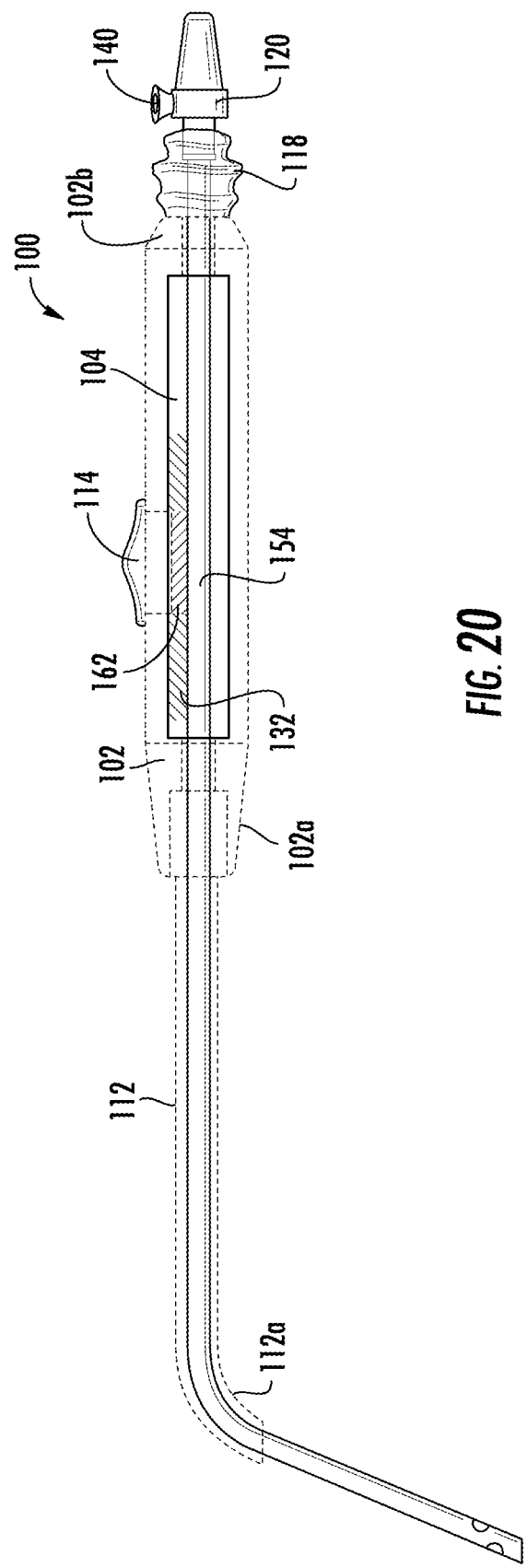
FIG. 20 is a side view of the tracheal and pharyngeal suction device of FIG. 19 without a connector.

The air duct 116 may be uncovered when the connector 106 is transitioned from the retracted position to the extended position. This prevents the treatment portion 108*a* from suctioning to the walls of the patient's mouth or throat before reaching the desired location in the patient. The air duct 116 may be covered when the connector 106 is transitioned from the extended position to the retracted position in order to perform the suctioning of the patient's throat and mouth. In further embodiments, as best illustrated in FIG. 19, the actuator 114 is solid and the port 120 includes a thumb port opening 140 that may be covered to complete the suction circuit. In still further embodiments, as best illustrated in FIG. 20, the tracheal and pharyngeal suction device 100 may include a main suction catheter 154 extending the length of the tracheal and pharyngeal suction device 100, a solid actuator 114, and a port 120 that includes a thumb port opening 140 that may be covered to complete the suction circuit. The main suction catheter may include a catheter-textured grip 132 and the actuator 114 may include an actuator textured grip 162.

In some embodiments, the tracheal and pharyngeal suction device 100 may include an actuator in the form of a spinning wheel 134, as best illustrated in FIGS. 9-11, with a spinning wheel duct or vent 136 extending through the diameter of the spinning wheel 134, a duct or vent opening 152, and a wheel-textured grip 148 positioned along the circumference of the spinning wheel 134. In some embodiments, the proximal suction catheter 108 may include a catheter-textured grip 132. In further embodiments, the tracheal and pharyngeal suction device 100 may include both a wheel-textured grip 148 and a catheter-textured grip 132 so that the spinning wheel 134 may cause the proximal suction catheter 108 to extend and retract from the oral suction tube 112 with minimal slipping. In some embodiments, the spinning wheel 134 and the proximal suction catheter 108 are aligned so that when the proximal suction catheter 108 is inserted to the desired location in the patient's mouth or throat cavity, the spinning wheel duct 136 aligns with a connector opening 150. When suction is then applied to the distal suction catheter 110 via the port 120, the suction is diverted from the treatment portion 108*a* of the proximal suction catheter 108 via the connector opening 150 and the spinning wheel duct 136 by connecting the interior cavity 104 to the atmosphere surrounding the handle 102. When a user covers the duct opening 152, the suction circuit is completed and suctioning may then occur at the treatment portion 108*a* of the proximal suction catheter 108. In some embodiments, an alignment device 138 may be attached to a proximal end 110*a* of the distal suction catheter 110 to ensure the alignment of the spinning wheel duct 136 and the connector opening 150.

In further embodiments, as best illustrated in FIGS. 10 and 11, a spinning wheel 134 may be included in a tracheal and pharyngeal suction device 100 that does not have a connector 106. Instead, the tracheal and pharyngeal suction device 100 may comprise a main suction catheter 154. In some embodiments, the main suction catheter 154 may include a catheter-textured grip 132. The main suction catheter 154 may have a catheter opening 146 that may align with the spinning wheel duct 136 when the proximal suction catheter 108 is inserted to the desired location in the patient's mouth or throat cavity so that suctioning may occur at the treatment portion 108*a* of the proximal suction catheter 108 when the duct opening 152 is covered.

In still further embodiments, as best illustrated in FIG. 11, the spinning wheel 134 and main suction catheter 154 may have no openings. Instead, the port 120 of the tracheal and pharyngeal suction device 100 may include a thumb port opening 140 that may be covered to complete the suction circuit.

In some embodiments, as best illustrated in FIGS. 12-14, the tracheal and pharyngeal suction device 100 may include an actuator 114 in the form of a continuous track 156 that includes a continuous band 142 and at least two wheels 144. The proximal suction catheter 108 may include a catheter-textured grip 132, and in some embodiments, the continuous band 142 may also be textured. The catheter-textured grip 132 enables the continuous track 156 to move the proximal suction catheter 108 with minimal slippage. The continuous band 142 includes two band openings 158 that align with each other and with the connector opening 150 when the treatment portion 108*a* of the proximal suction catheter 108 reaches the desired extended position (e.g., the desired or pre-set location in the patient's mouth or throat cavity) to connect the connector 106 to the atmosphere surrounding the handle 102 and thereby divert suction from the treatment portion 108*a* of the proximal suction catheter 108. A user may then cover the band openings 158 to complete the suction circuit, and suctioning may then occur at the treatment portion 108a of the proximal suction catheter 108.

In further embodiments, as best illustrated in FIGS. 13 and 14, the tracheal and pharyngeal suction device 100 may not include a connector 106. Instead, the tracheal and pharyngeal suction device 100 may comprise the main suction catheter 154. In some embodiments, the main suction catheter 154 may include the catheter-textured grip 132. The main suction catheter 154 may have the catheter opening 146 that may align with the two band openings 158 when the treatment portion 108a of the proximal suction catheter 108 reaches the extended position.

In still further embodiments, as best illustrated in FIG. 14, the continuous track 156 and the main suction catheter 154 may have no openings. Instead, the port 120 of the tracheal and pharyngeal suction device 100 may include a thumb port opening 140 that may be covered to complete the suction circuit.

In some embodiments, as best illustrated in FIGS. 15-17, the tracheal and pharyngeal suction device 100 may not include an actuator 114. Instead, the handle 102 may comprise an opening 160 that allows the user to access and move the proximal suction catheter 108, the distal suction catheter 110, and/or the main suction catheter 154 directly using a finger. In certain embodiments that comprise the connector 106, as best illustrated in FIG. 15, when the treatment portion 108a of the proximal suction catheter 108 reaches the desired location in the patient's mouth or throat cavity, the user may cover a connector opening 150 within the connector 106 to complete the suction circuit.

In further embodiments that do not comprise the connector 106, as best illustrated in FIGS. 16 and 17, the main suction catheter 154 with the catheter opening 146 may be used, and a user may cover the catheter opening 146 to complete the suction circuit. In still further embodiments, as best illustrated in FIG. 17, the main suction catheter 154 may not have any openings, but the port 120 of the tracheal and pharyngeal suction device 100 may include a thumb port opening 140 that may be covered to complete the suction circuit.

Figure 26:
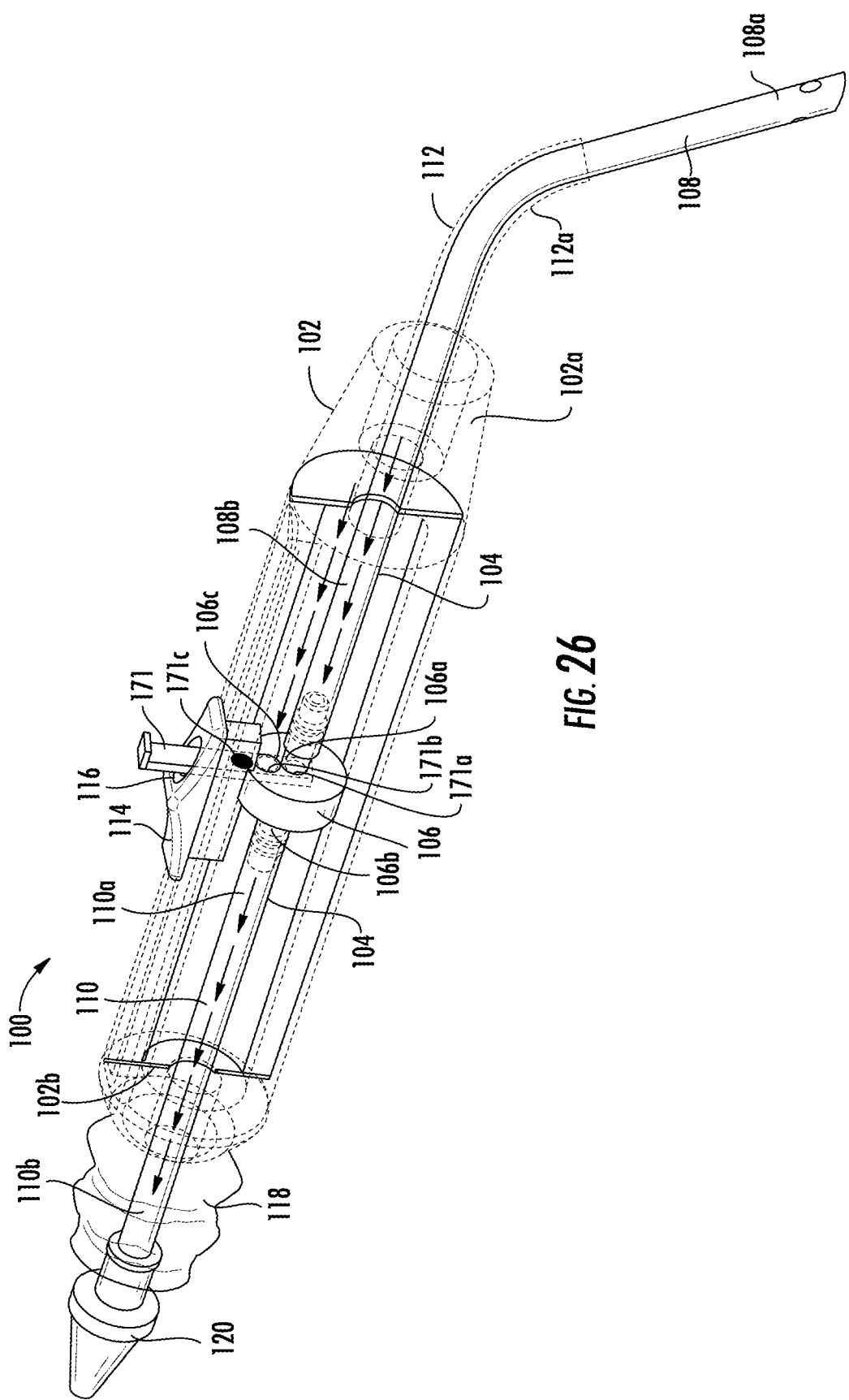
FIG. 26 is a perspective view of the tracheal and pharyngeal suction device of FIG. 24.

In some embodiments, as best illustrated in FIGS. 24 and 26, the handle 102 may include a sliding member 171 extending from inside the connector 106 through the actuator 114 and out the air duct 116. The sliding member 171 may include any number of holes and any combination of open and closed holes. As best illustrated in FIG. 24A, the sliding member 117 may have two closed holes 171a and 171c and one open hole 171b, where the two closed holes 171a and 171c are located on either side of the open hole 171b. As best illustrated in FIG. 24B, the sliding member 117 may have two open holes 171a and 171b and one closed hole 171c, where the one closed hole 171c is located above the two open holes 171a and 171b. In some embodiments, the sliding member 171 may be manufactured to have only one or two open holes. In further embodiments the sliding member 171 may be manufactured to have three open holes and a rubber gasket, or any other suitable insert or covering, may be attached to or inserted into one or more of the open holes 171a, 171b, or 171c in order to close the open holes.

Figure 25:
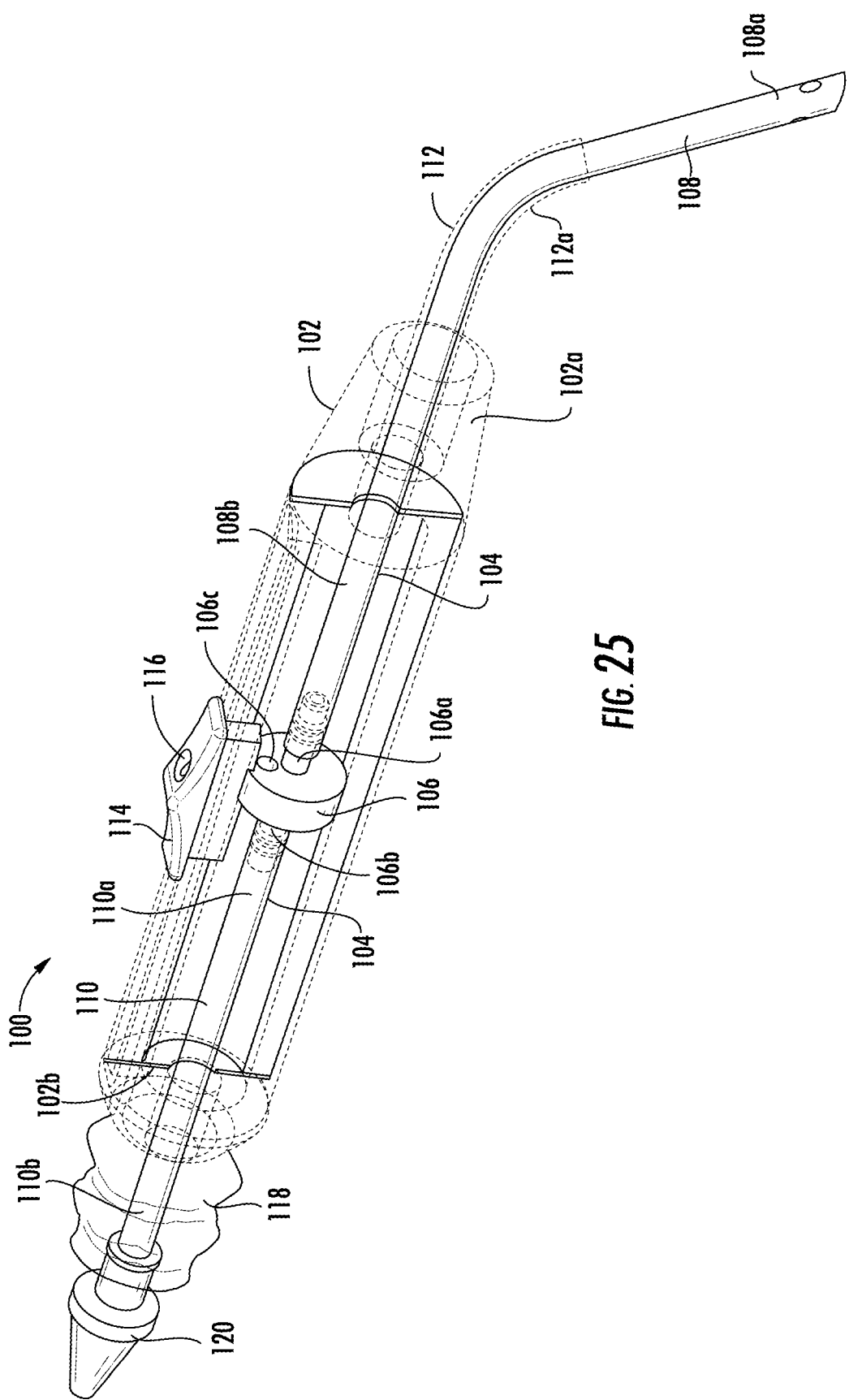
FIG. 25 is a perspective view of the tracheal and pharyngeal suction device of FIG. 1 with a connector opening.

In some embodiments, as best illustrated in FIG. 25, the connector 106 may include a connector opening 106c positioned just above the proximal end 106a of the connector 106. The sliding member 171 may be positioned in an up position, as best illustrated in FIGS. 24 and 26, or a down position to control the suction of the tracheal and pharyngeal suction device. The suction circuit may be completed in different ways depending on the positioning of the sliding member 171 and the open and closed nature of the holes 171a, 171b, and 171c.

For example, a sliding member 171 in the up position with one open hole 171b in between two closed holes 171a and 171c may permit suctioning of the interior cavity 104 by blocking the opening to the proximal end 106a of the connector 106. This may allow for a more efficient method of sterilizing the interior cavity 104. A user may move the sliding member 171 to the down position which may permit suctioning to occur at the treatment portion 108a of the proximal suction catheter 108 by having closed hole 171c block the connector opening 106c and having the user cover the air duct 116.

In further embodiments, as best illustrated in FIG. 26, a sliding member 171 in the up position with two open holes 171a and 171b below one closed hole 171c may permit suctioning to occur both inside the interior cavity 104 as well as at the treatment portion 108a of the proximal suction catheter 108, thus enabling dual suctioning to occur. Dual suctioning may permit the tracheal and pharyngeal suction device to be used as an oral suction device. A user may move the sliding member 171 to the down position which may permit suctioning to occur at the treatment portion 108a of the proximal suction catheter 108 by blocking the connector opening 106c and the user covering the air duct 116, thus enabling normal suctioning through the treatment portion 108a to occur.

In some embodiments, the tracheal and pharyngeal suction device 100 may include an adjustable stop 124, as best illustrated in FIG. 7. The adjustable stop may be an attachment that is inserted into a stopper indention 126 along the path of the actuator, a ring that may be placed around the handle 102, or any other suitable means for preventing the actuator 114 from traveling beyond the location of the adjustable stop 124. The adjustable stop 124 may be made of plastic, rubber, or any other suitable material. In some embodiments, the adjustable stop 124 may aid a user in minimizing potential injury to a patient by preventing the user from moving the actuator 114 too far in the proximal direction of the handle 102, which in turn prevents the proximal suction catheter 108 from extending too far into the patient's mouth or throat cavity.

Figure 6:
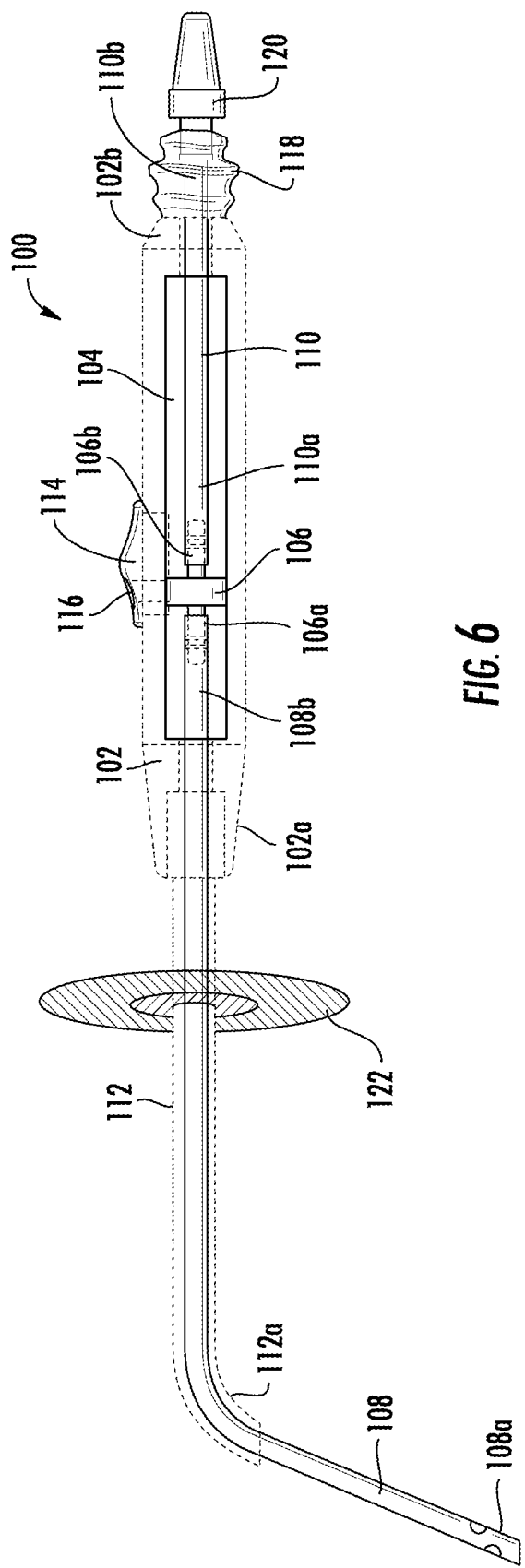
FIG. 6 is a side view of the tracheal and pharyngeal suction device of FIG. 1 with a guard attached.

The tracheal and pharyngeal suction device 100 may include a guard 122, as best illustrated in FIG. 6, attached to the oral suction tube 112. In some embodiments, the guard 122 may be circular, rectangular, oval, or any other suitable shape. In further embodiments, a user may slide the guard 122 into the desired position on the oral suction tube 112. In still other embodiments, the guard 122 may include a hinge on one side and a clasp on the other to enable the guard 122 to be positioned on the oral suction tube 112. The guard 122 may be positioned on the oral suction tube 112 to prevent the tracheal and pharyngeal suction device from being inserted too far into the patient's mouth or throat cavity.

In use, the tracheal and pharyngeal suction device 100 is designed to improve oral suctioning, oral tracheal suctioning, and oral pharyngeal suctioning. A user begins each process by inserting the handle 102 of the tracheal and pharyngeal suction device 100 into the patient's mouth. The user will stop inserting the handle 102 when a proximal end 112a of the oral suction tube 112 is approximately 7.62 centimeters (3 inches) away from the pharyngeal region of the patient's throat and approximately 15.24 centimeters (6 inches) away from the tracheal of the patient. The user may then extend the treatment portion 108a of the proximal suction catheter 108 beyond the end of the handle until it reaches the desired location in the patient's throat. In some embodiments, the treatment portion 108a of the proximal suction catheter 108 may be extended by moving the actuator 114 in the direction of the proximal end 102a of the handle. In other embodiments, the treatment portion 108a of the proximal suction catheter 108 may be extended without using the actuator 114. For oral pharyngeal suctioning, the treatment portion 108a will be extended approximately 7.62 centimeters (3 inches) when used on a patient of average size to reach the pharyngeal region of the patient's throat. For oral tracheal suctioning, the treatment portion 108a will be extended approximately 15.24 centimeters (6 inches) when used on a patient of average size to reach the trachea of the patient. However, one of skill in the relevant art will understand that the distance to reach the desired location in the patient's throat will vary based on the size of the patient.

Once the treatment portion 108a is in the desired location, the user may begin suctioning by covering the air duct 116 to engage suctioning through the proximal suction catheter. While the suctioning is engaged, the user may remove the tracheal and pharyngeal suction device 100 from the mouth of the patient. In some embodiments, as the user is removing the tracheal and pharyngeal suction device, the proximal suction catheter 108 may be simultaneously retracted into the oral suction tube 112.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A tracheal and pharyngeal suction device comprising:
a handle comprising an interior cavity within the handle and an actuator comprising a proximal side and a distal side positioned at least partially along an outer surface of the handle;
a connector positioned within the interior cavity and moveable along at least a portion of a length of the interior cavity between a retracted position and an extended position;
a proximal suction catheter having a coupling portion and a treatment portion, wherein the coupling portion is coupled to a proximal side of the connector; and
a distal suction catheter coupled to a distal side of the connector;
wherein the treatment portion of the proximal suction catheter extends beyond a proximal end of the handle when the connector is in the extended position;
wherein the proximal suction catheter and the distal suction catheter are separate components;
wherein the actuator is coupled with the connector and is configured to cause the connector to translate between the retracted position and the extended position; and
wherein a duct extends through the proximal side of the actuator between a hollow interior of the connector and the atmosphere surrounding the handle, and the duct comprises a duct opening that is limited to the proximal side of the actuator.

2. The tracheal and pharyngeal suction device of claim 1, wherein the treatment portion of the proximal suction catheter is configured to be positioned within at least one of a tracheal region and a pharyngeal region of a patient's throat when the handle is positioned within a patient's mouth and the connector is in the extended position.

3. The tracheal and pharyngeal suction device of claim 1, wherein the connector travels a distance ranging from 0.25 inches to 10 inches between the retracted position and the extended position.

4. The tracheal and pharyngeal suction device of claim 1, wherein the handle further comprises an oral suction tube coupled to the proximal end of the handle, wherein at least the coupling portion of the proximal suction catheter is positioned within the oral suction tube.

5. The tracheal and pharyngeal suction device of claim 4, wherein the treatment portion of the proximal suction catheter is retracted within the oral suction tube when the connector is in the retracted position.

6. The tracheal and pharyngeal suction device of claim 4, wherein the treatment portion of the proximal suction catheter extends a distance ranging from 0.25 inches to 10 inches outside of the oral suction tube when the connector is in the extended position.

7. The tracheal and pharyngeal suction device of claim 4, wherein the oral suction tube comprises a guard coupled to an outer surface of the oral suction tube.

8. The tracheal and pharyngeal suction device of claim 1, wherein the actuator comprises a thumb switch, a spinning wheel, or a continuous track.

9. The tracheal and pharyngeal suction device of claim 1, wherein the duct opening comprises a circular opening on a surface of the actuator.

10. The tracheal and pharyngeal suction device of claim 1, wherein the duct is manually uncovered by a user when the connector is transitioned from the retracted position to the extended position and is manually covered by the user when the connector is transitioned from the extended position to the retracted position.

11. The tracheal and pharyngeal suction device of claim 1, wherein, when the distal suction catheter is coupled to a vacuum source, the duct diverts suction away from the proximal suction catheter when the duct is uncovered and applies suction to the proximal suction catheter when the duct is covered.

12. The tracheal and pharyngeal suction device of claim 1, wherein the handle comprises an adjustable stop configured to adjust a location of the extended position by preventing the connector from traveling beyond the location of the adjustable stop in a proximal direction of the handle.

13. The tracheal and pharyngeal suction device of claim 1, wherein the proximal suction catheter is detachable from the connector of the handle.

14. The tracheal and pharyngeal suction device of claim 1, wherein the handle comprises multiple separable components, wherein an extender is positioned between the multiple separable components.

15. The tracheal and pharyngeal suction device of claim 1, wherein the actuator is configured to move the connector from the retracted position to the extended position by a pressure exerted on the distal side of the actuator and is configured to move the connector from the extended position to the retracted position by a pressure exerted on the proximal side of the actuator.

16. A method of using a tracheal and pharyngeal suction device that comprises a handle; a connector moveable along at least a portion of a length of an interior cavity in the handle and including an actuator comprising a proximal side and a distal side positioned on an outer surface of the handle; a duct extending through the proximal side of the actuator between a hollow interior of the connector and the atmosphere surrounding the handle, wherein the duct comprises a duct opening that is limited to the proximal side of the actuator; a proximal suction catheter having a treatment portion and a coupling portion, wherein the coupling portion is coupled to a proximal side of the connector; and a distal suction catheter coupled to a distal side of the connector, wherein the proximal suction catheter and the distal suction catheter are separate components, the method comprising:

inserting the handle into a patient's mouth;
extending at least the treatment portion of the proximal suction catheter beyond a proximal end of the handle to a desired distance within a patient's throat by applying a pressure to the distal side of the actuator as the duct opening remains uncovered to move the actuator along the outer surface of the handle;
covering the duct opening to engage suction through the proximal suction catheter; and
retracting at least the treatment portion of the proximal suction catheter by moving the actuator along the outer surface of the handle as the duct opening remains covered.

17. The method of claim 16, further comprising measuring the patient's throat using a standardized unit of measurement to find the desired distance.

18. The method of claim 16, further comprising attaching an adjustable stop to prevent the connector from traveling beyond a location of the adjustable stop in a proximal direction of the handle.

19. The method of claim 16, further comprising retracting at least the treatment portion of the proximal suction catheter as a user removes the handle from the patient's mouth.

20. A tracheal and pharyngeal suction system comprising:
a tracheal and pharyngeal suction device comprising:
a handle comprising an interior cavity within the handle;
a connector positioned within the interior cavity and moveable along at least a portion of a length of the interior cavity between a retracted position and an extended position;
a proximal suction catheter having a coupling portion and a treatment portion, wherein the coupling portion is coupled to a proximal side of the connector; and
a distal suction catheter coupled to a distal side of the connector;
wherein the proximal suction catheter and the distal suction catheter are separate components;
an oral suction tube coupled to a proximal end of the handle;
an actuator comprising a proximal side and a distal side positioned along an outer surface of the handle and coupled to the connector, wherein the actuator comprises a duct extending through the proximal side of the actuator between a hollow interior of the connector and the atmosphere surrounding the handle, and the duct comprises a duct opening that is limited to the proximal side of the actuator;
an adjustable stop configured to adjust a location of the extended position by preventing the actuator from traveling beyond the location of the adjustable stop in a proximal direction of the handle;
a port coupled to the distal suction catheter;
a covering coupled to a distal end of the handle and to the port;
a guard attachable to the oral suction tube to prevent the handle from being inserted too far into a patient's mouth;
a measurement device; and
an extender attachable to the handle to allow for the proximal suction catheter to be extended different lengths.

* * * * *